US010231609B2

(12) United States Patent
Poll et al.

(10) Patent No.: US 10,231,609 B2
(45) Date of Patent: Mar. 19, 2019

(54) SYSTEMS AND METHODS FOR OPTIMIZING AND MAINTAINING VISUALIZATION OF A SURGICAL FIELD DURING THE USE OF SURGICAL SCOPES

(71) Applicant: Floshield, Inc., Cupertino, CA (US)

(72) Inventors: Wayne L. Poll, New Albany, OH (US); Matthew J. Huddleston, Galena, OH (US); Caroline M. Crisafulli, Columbus, OH (US); Adam Landis, Reynoldsburg, OH (US); Gregory P. Drach, Liberty Township, OH (US)

(73) Assignee: Floshield, Inc., Cupertino, CA (US)

( * ) Notice: Subject to any disclaimer, the term of this patent is extended or adjusted under 35 U.S.C. 154(b) by 0 days.

(21) Appl. No.: 14/490,501

(22) Filed: Sep. 18, 2014

(65) Prior Publication Data
US 2015/0005582 A1    Jan. 1, 2015

Related U.S. Application Data

(63) Continuation of application No. 12/653,148, filed on Dec. 9, 2009, now Pat. No. 8,888,689, which is a (Continued)

(51) Int. Cl.
*A61B 1/00* (2006.01)
*A61B 1/12* (2006.01)
(Continued)

(52) U.S. Cl.
CPC .......... *A61B 1/127* (2013.01); *A61B 1/00091* (2013.01); *A61B 1/00135* (2013.01);
(Continued)

(58) Field of Classification Search
CPC ............ A61B 1/00068; A61B 1/00112; A61B 1/00114; A61B 1/00117; A61B 1/00119;
(Continued)

(56) References Cited

U.S. PATENT DOCUMENTS 3,373,736 A   3/1968   Fiore et al.
D230,727 S    3/1974   Richman
(Continued)

FOREIGN PATENT DOCUMENTS

EP    0664101 A1   7/1995
EP    0790652 A1   8/1997
(Continued)

OTHER PUBLICATIONS

Poll et al.; Design U.S. Appl. No. 29/329,224 entitled "Manifold Coupling," filed Dec. 10, 2008 (now abandoned).
(Continued)

*Primary Examiner* — Ryan Henderson
(74) *Attorney, Agent, or Firm* — Shay Glenn LLP

(57) ABSTRACT

A method of defogging and cleaning a laparoscope includes: (1) inserting a laparoscope into a sheath; (2) inserting the laparoscope and sheath into a body cavity; (3) providing gas to a plurality of gas lumens within a wall of the sheath such that the gas flows through the gas lumens and over a lens of the laparoscope to defog the lens while the laparoscope is in the body cavity; and (4) providing a fluid comprising a surface-active agent to a fluid lumen within the wall of the sheath such that the fluid flows through the fluid lumen and over the lens to clean the lens while the laparoscope is in the body cavity.

11 Claims, 25 Drawing Sheets

Related U.S. Application Data continuation-in-part of application No. 11/765,340, filed on Jun. 19, 2007, now Pat. No. 9,050,036.

(60) Provisional application No. 61/121,514, filed on Dec. 10, 2008, provisional application No. 61/170,864, filed on Apr. 20, 2009.

(51) Int. Cl.
    *A61B 1/012*     (2006.01)
    *A61B 1/015*     (2006.01)
    *A61B 1/313*     (2006.01)
    *A61B 17/34*     (2006.01)
    *A61M 13/00*     (2006.01)

(52) U.S. Cl.
    CPC .............. *A61B 1/126* (2013.01); *A61B 1/313* (2013.01); *A61B 1/3132* (2013.01); *A61B 17/3474* (2013.01); *A61M 13/003* (2013.01); *A61B 2017/347* (2013.01); *A61M 2202/0225* (2013.01); *A61M 2205/3344* (2013.01)

(58) Field of Classification Search
    CPC ............ A61B 1/00121; A61B 1/00124; A61B 1/00126; A61B 1/00128; A61B 1/00135; A61B 1/00142; A61B 1/015; A61B 1/12; A61B 1/125
    USPC ................. 600/121–125, 132, 156–159, 169, 600/175–177; 604/22–26, 43–45
    See application file for complete search history.

(56) References Cited

U.S. PATENT DOCUMENTS

| | | |
|---|---|---|
| 4,207,874 A | 6/1980 | Choy |
| 4,279,246 A | 7/1981 | Chikama |
| 4,281,646 A | 8/1981 | Kinoshita |
| 4,436,087 A | 3/1984 | Ouchi |
| D277,408 S | 1/1985 | Kubokawa et al. |
| D277,505 S | 2/1985 | Kubokawa et al. |
| 4,497,550 A | 2/1985 | Ouchi et al. |
| 4,537,209 A | 8/1985 | Sasa |
| D280,929 S | 10/1985 | Lystager |
| 4,548,197 A | 10/1985 | Kinoshita |
| 4,552,130 A | 11/1985 | Kinoshita |
| D284,028 S | 5/1986 | Seager |
| 4,598,698 A | 7/1986 | Siegmund |
| 4,616,169 A | 10/1986 | Proffitt |
| 4,617,013 A | 10/1986 | Betz |
| 4,633,855 A | 1/1987 | Baba |
| 4,637,814 A | 1/1987 | Leiboff |
| 4,646,722 A | 3/1987 | Silverstein et al. |
| 4,735,603 A | 4/1988 | Goodson et al. |
| 4,741,326 A | 5/1988 | Sidall et al. |
| 4,748,970 A * | 6/1988 | Nakajima .......... A61B 1/00068 600/113 |
| 4,760,838 A | 8/1988 | Fukuda |
| 4,773,413 A | 9/1988 | Hussein et al. |
| 4,794,911 A | 1/1989 | Okada |
| 4,800,869 A | 1/1989 | Nakajima |
| 4,877,016 A | 10/1989 | Kantor et al. |
| 4,941,872 A | 7/1990 | Felix et al. |
| 4,973,321 A | 11/1990 | Michelson |
| 4,991,565 A | 2/1991 | Takahashi et al. |
| 4,998,527 A | 3/1991 | Meyer |
| 5,009,655 A | 4/1991 | Daignault, Jr. et al. |
| 5,019,054 A | 5/1991 | Clement et al. |
| 5,027,791 A | 7/1991 | Takahashi |
| 5,050,585 A | 9/1991 | Takahashi |
| 5,133,336 A | 7/1992 | Savitt et al. |
| 5,144,942 A | 9/1992 | Decarie et al. |
| 5,147,292 A | 9/1992 | Kullas et al. |
| 5,163,927 A | 11/1992 | Woker et al. |
| 5,167,220 A | 12/1992 | Brown |
| 5,201,908 A | 4/1993 | Jones |
| 5,207,213 A | 5/1993 | Auhll et al. |
| 5,225,001 A | 7/1993 | Manni et al. |
| 5,279,549 A | 1/1994 | Ranford |
| D346,023 S | 4/1994 | Stewart, Sr. |
| 5,306,272 A | 4/1994 | Cohen et al. |
| 5,312,400 A | 5/1994 | Bales et al. |
| 5,313,934 A | 5/1994 | Wiita et al. |
| 5,320,091 A | 6/1994 | Grossi et al. |
| 5,322,070 A | 6/1994 | Goodman et al. |
| 5,328,458 A | 7/1994 | Sekino et al. |
| 5,336,170 A | 8/1994 | Salerno et al. |
| 5,339,800 A | 8/1994 | Wiita et al. |
| 5,359,991 A | 11/1994 | Takahashi et al. |
| 5,364,407 A | 11/1994 | Poll |
| 5,386,817 A | 2/1995 | Jones |
| 5,392,766 A | 2/1995 | Masterson et al. |
| 5,400,767 A | 3/1995 | Murdoch |
| 5,448,891 A | 9/1995 | Nakagiri et al. |
| 5,448,990 A | 9/1995 | De Faria Correa |
| 5,464,008 A | 11/1995 | Kim |
| 5,468,240 A | 11/1995 | Gentelia et al. |
| D369,862 S | 5/1996 | Stewart, Jr. |
| 5,514,074 A | 5/1996 | Yabe et al. |
| 5,514,084 A | 5/1996 | Fisher |
| 5,518,502 A * | 5/1996 | Kaplan ................. A61B 1/127 600/156 |
| 5,562,600 A | 10/1996 | Matsuno |
| 5,563,737 A | 10/1996 | Kamrat |
| 5,569,157 A | 10/1996 | Nakazawa et al. |
| 5,575,753 A | 11/1996 | Yabe et al. |
| 5,575,756 A | 11/1996 | Karasawa et al. |
| 5,605,532 A | 2/1997 | Schermerhorn |
| 5,630,795 A | 5/1997 | Kuramoto et al. |
| 5,637,075 A | 6/1997 | Kikawada |
| 5,647,840 A | 7/1997 | D'Amelio et al. |
| 5,697,888 A * | 12/1997 | Kobayashi et al. .......... 600/159 |
| 5,722,933 A | 3/1998 | Yabe et al. |
| 5,746,695 A | 5/1998 | Yasui et al. |
| 5,788,628 A | 8/1998 | Matsuno et al. |
| 5,857,961 A | 1/1999 | Vanden Hoek et al. |
| 5,863,286 A | 1/1999 | Yabe et al. |
| 5,865,730 A | 2/1999 | Fox et al. |
| 5,868,663 A | 2/1999 | Katsurada et al. |
| 5,869,107 A | 2/1999 | Shimizu et al. |
| 5,894,369 A | 4/1999 | Akiba et al. |
| 5,922,105 A | 7/1999 | Fujii et al. |
| 5,954,637 A | 9/1999 | Francis |
| 5,957,888 A | 9/1999 | Hinchliffe |
| 5,989,183 A | 11/1999 | Reisdorf et al. |
| 6,017,333 A | 1/2000 | Bailey |
| 6,040,053 A | 3/2000 | Scholz et al. |
| 6,071,606 A | 6/2000 | Yamazaki et al. |
| D428,487 S | 7/2000 | Renner et al. |
| 6,096,026 A | 8/2000 | Schultz |
| 6,110,103 A | 8/2000 | Donofrio |
| 6,110,259 A | 8/2000 | Schultz et al. |
| 6,113,586 A | 9/2000 | Ouchi |
| 6,117,070 A | 9/2000 | Akiba |
| 6,126,592 A | 10/2000 | Proch et al. |
| 6,149,659 A | 11/2000 | Ahmed |
| 6,156,409 A | 12/2000 | Doushita et al. |
| 6,176,825 B1 | 1/2001 | Chin et al. |
| 6,206,825 B1 | 3/2001 | Tsuyuki |
| 6,234,635 B1 | 5/2001 | Seitzinger et al. |
| 6,282,442 B1 | 8/2001 | DeStefano et al. |
| 6,293,909 B1 | 9/2001 | Chu et al. |
| 6,299,592 B1 | 10/2001 | Zander |
| 6,306,932 B1 | 10/2001 | Yamamoto et al. |
| 6,354,992 B1 | 3/2002 | Kato |
| 6,361,492 B1 | 3/2002 | Santilli |
| 6,383,134 B1 | 5/2002 | Santilli |
| 6,409,657 B1 | 6/2002 | Kawano |
| 6,425,535 B1 | 7/2002 | Akiba |
| 6,447,446 B1 | 9/2002 | Smith et al. |
| 6,582,357 B2 | 6/2003 | Ouchi et al. |
| 6,589,316 B1 | 7/2003 | Schultz et al. |
| D481,126 S | 10/2003 | Hayamizu |
| 6,645,197 B2 | 11/2003 | Garrison et al. |

(56) References Cited

U.S. PATENT DOCUMENTS

| | | |
|---|---|---|
| D484,594 S | 12/2003 | Hayamizu |
| D486,910 S | 2/2004 | Hayamizu et al. |
| 6,695,772 B1 | 2/2004 | Bon et al. |
| 6,699,185 B2 | 3/2004 | Gminder et al. |
| 6,712,479 B1 | 3/2004 | Seitzinger et al. |
| 6,712,757 B2 | 3/2004 | Becker et al. |
| 6,712,759 B2 | 3/2004 | Muller |
| 6,752,755 B2 | 6/2004 | Akiba |
| 6,755,782 B2 | 6/2004 | Ogawa |
| D493,529 S | 7/2004 | Hayamizu et al. |
| 6,764,445 B2 | 7/2004 | Ramans et al. |
| 6,780,516 B2 | 8/2004 | Chen |
| 6,783,845 B2 | 8/2004 | Zhang et al. |
| D498,846 S | 11/2004 | Hayamizu et al. |
| 6,814,697 B2 | 11/2004 | Ouchi |
| 6,857,436 B2 | 2/2005 | Labib et al. |
| 6,858,005 B2 | 2/2005 | Ohline et al. |
| 6,882,236 B2 | 4/2005 | Dinn et al. |
| 6,889,400 B2 | 5/2005 | Kawazoe et al. |
| 6,921,362 B2 | 7/2005 | Ouchi |
| 6,921,380 B1 | 7/2005 | Epstein et al. |
| 6,977,053 B2 | 12/2005 | Mukasa et al. |
| 6,984,204 B2 | 1/2006 | Akiba |
| 6,989,183 B2 | 1/2006 | McKillip |
| 7,074,180 B2 | 7/2006 | Bertolero et al. |
| 7,080,641 B2 | 7/2006 | Gomez |
| 7,087,013 B2 | 8/2006 | Belson et al. |
| 7,150,713 B2 | 12/2006 | Shener et al. |
| D534,655 S | 1/2007 | Iranyi et al. |
| D535,743 S | 1/2007 | Williams |
| 7,169,167 B2 | 1/2007 | Chu |
| 7,198,599 B2 | 4/2007 | Goto et al. |
| 7,223,231 B2 | 5/2007 | Akiba |
| 7,250,028 B2 | 7/2007 | Julian et al. |
| 7,270,670 B1 | 9/2007 | Yencho |
| 7,341,556 B2 | 3/2008 | Shalman |
| D573,711 S | 7/2008 | Johnson et al. |
| 7,413,543 B2 | 8/2008 | Banik et al. |
| 7,435,218 B2 | 10/2008 | Krattiger et al. |
| D600,807 S | 9/2009 | Dienst et al. |
| D613,403 S | 4/2010 | Poll et al. |
| 7,803,109 B2 | 9/2010 | Gomez |
| 7,803,144 B1 | 9/2010 | Vollrath |
| 7,927,271 B2 | 4/2011 | Dimitriou et al. |
| 8,047,215 B1 | 11/2011 | Sasaki |
| 8,062,214 B2 | 11/2011 | Shener et al. |
| 8,075,481 B2 | 12/2011 | Park et al. |
| 8,096,944 B2 | 1/2012 | Harrel |
| 8,226,549 B2 | 7/2012 | Kumar et al. |
| 8,419,624 B2 | 4/2013 | James et al. |
| 8,517,921 B2 | 8/2013 | Tremaglio et al. |
| 8,545,395 B2 | 10/2013 | Akahoshi et al. |
| 8,888,689 B2 | 11/2014 | Poll et al. |
| 2001/0011162 A1 | 8/2001 | Epstein |
| 2002/0022762 A1 | 2/2002 | Beane et al. |
| 2002/0058858 A1 | 5/2002 | Ogura et al. |
| 2002/0072652 A1 | 6/2002 | Berci et al. |
| 2002/0091304 A1 | 7/2002 | Ogura et al. |
| 2002/0193806 A1 | 12/2002 | Moenning et al. |
| 2003/0200738 A1 | 10/2003 | Booth |
| 2004/0034339 A1 | 2/2004 | Stoller et al. |
| 2004/0059363 A1 | 3/2004 | Alvarez et al. |
| 2004/0082915 A1 | 4/2004 | Kadan |
| 2004/0204671 A1 | 10/2004 | Stubbs et al. |
| 2004/0216468 A1 | 11/2004 | Hatcher |
| 2005/0043683 A1 | 2/2005 | Ravo |
| 2005/0059981 A1 | 3/2005 | Poll |
| 2005/0065405 A1 | 3/2005 | Hasegawa |
| 2005/0080342 A1 | 4/2005 | Gilreath et al. |
| 2005/0113797 A1 | 5/2005 | Ott et al. |
| 2005/0119528 A1 | 6/2005 | Weinberg |
| 2005/0137529 A1 | 6/2005 | Mantell |
| 2005/0154355 A1 | 7/2005 | Gross et al. |
| 2005/0159765 A1 | 7/2005 | Moutafis et al. |
| 2005/0171467 A1 | 8/2005 | Landman |
| 2005/0171528 A1 | 8/2005 | Sartor et al. |
| 2005/0203342 A1 | 9/2005 | Kucklick et al. |
| 2005/0234301 A1 | 10/2005 | Gomez |
| 2005/0261553 A1 | 11/2005 | Swain et al. |
| 2006/0020165 A1 | 1/2006 | Adams |
| 2006/0041186 A1 | 2/2006 | Vancaillie |
| 2006/0047184 A1 | 3/2006 | Banik et al. |
| 2006/0052661 A1 | 3/2006 | Gannot et al. |
| 2006/0069306 A1 | 3/2006 | Banik et al. |
| 2006/0252993 A1 | 11/2006 | Freed et al. |
| 2006/0270910 A1 | 11/2006 | Davis |
| 2007/0088275 A1 | 4/2007 | Stearns et al. |
| 2007/0179432 A1 | 8/2007 | Bar et al. |
| 2007/0182842 A1 | 8/2007 | Sonnenschein et al. |
| 2007/0203474 A1 | 8/2007 | Ryan et al. |
| 2007/0282253 A1 | 12/2007 | Sasaki |
| 2007/0289449 A1 | 12/2007 | Roberts et al. |
| 2007/0299310 A1 | 12/2007 | Phillips |
| 2008/0021277 A1 | 1/2008 | Stefanchik et al. |
| 2008/0051631 A1 | 2/2008 | Dejima et al. |
| 2008/0058591 A1 | 3/2008 | Saadat et al. |
| 2008/0081948 A1 | 4/2008 | Weisenburgh et al. |
| 2008/0082084 A1 | 4/2008 | Roberts et al. |
| 2008/0086704 A1 | 4/2008 | Aravamudan |
| 2008/0108871 A1 | 5/2008 | Mohr |
| 2008/0161646 A1 | 7/2008 | Gomez |
| 2008/0188715 A1 | 8/2008 | Fujimoto |
| 2008/0200765 A1 | 8/2008 | Mondschein |
| 2008/0208128 A1 | 8/2008 | Guo et al. |
| 2008/0249362 A1 | 10/2008 | Jiang et al. |
| 2008/0255419 A1 | 10/2008 | Kendale et al. |
| 2008/0255424 A1 | 10/2008 | Durgin et al. |
| 2008/0319266 A1 | 12/2008 | Poll et al. |
| 2009/0018602 A1 | 1/2009 | Mitelberg et al. |
| 2009/0113644 A1 | 5/2009 | Heck |
| 2009/0215018 A1 | 8/2009 | Edmondson et al. |
| 2009/0234193 A1 | 9/2009 | Weisenburgh et al. |
| 2009/0253962 A1 | 10/2009 | Fernandez et al. |
| 2009/0253964 A1 | 10/2009 | Miyamoto |
| 2009/0253965 A1* | 10/2009 | Miyamoto .................. 600/157 |
| 2010/0010310 A1 | 1/2010 | Weisenburgh et al. |
| 2010/0168520 A1 | 7/2010 | Poll et al. |
| 2010/0331856 A1 | 12/2010 | Carlson et al. |
| 2012/0022331 A1 | 1/2012 | Poll et al. |
| 2012/0165610 A1 | 6/2012 | Poll et al. |
| 2012/0184897 A1 | 7/2012 | Poll |
| 2012/0197084 A1 | 8/2012 | Drach et al. |
| 2012/0310147 A1 | 12/2012 | Poll et al. |
| 2013/0231606 A1 | 9/2013 | Stearns et al. |
| 2013/0317295 A1 | 11/2013 | Morse |
| 2016/0089006 A1 | 3/2016 | Poll et al. |
| 2016/0174828 A1 | 6/2016 | Drach et al. |

FOREIGN PATENT DOCUMENTS

| | | |
|---|---|---|
| EP | 1188415 A2 | 3/2002 |
| JP | 59-203534 | 11/1984 |
| JP | 61-168328 | 7/1986 |
| JP | 05-103756 A | 4/1993 |
| JP | 05-199979 | 8/1993 |
| JP | H07-275185 A | 10/1995 |
| JP | 09-135804 | 5/1997 |
| JP | 2000-225093 | 8/2000 |
| JP | 2004-267583 A | 9/2004 |
| JP | 2005-110978 | 4/2005 |
| JP | 2009-240596 A | 10/2009 |
| WO | WO92/10969 A1 | 7/1992 |
| WO | WO92/22238 A1 | 12/1992 |
| WO | WO2005/002210 A1 | 1/2005 |
| WO | WO2005/009227 A1 | 2/2005 |
| WO | WO2005/115221 A1 | 12/2005 |
| WO | WO2006/014814 A1 | 2/2006 |
| WO | WO2008/030256 A1 | 3/2008 |
| WO | WO2008/077080 A2 | 6/2008 |
| WO | WO2008/128142 A2 | 10/2008 |
| WO | WO2008/130582 A2 | 10/2008 |
| WO | WO2009/073577 A2 | 6/2009 |
| WO | WO2010/042913 A2 | 4/2010 |

(56) References Cited

FOREIGN PATENT DOCUMENTS

| WO | WO2010/042915 A2 | 4/2010 |
|----|------------------|--------|
| WO | WO2011/041387 A1 | 4/2011 |
| WO | WO2011/044448 A2 | 4/2011 |

OTHER PUBLICATIONS

Poll et al.; Design U.S. Appl. No. 29/329,225 entitled "Sheath Manifold for Maintaining Surgical Scope Visualization," filed Dec. 10, 2008 (now abandoned).

Poll et al.; Design U.S. Appl. No. 29/329,221 entitled "Handle for Maintaining Surgical Scope Visualization," filed Dec. 10, 2008 (now abandoned).

Poll et al.; Design U.S. Appl. No. 29/335,699 entitled "Surgical Scope Stabilizer," filed Apr. 20, 2009 (now abandoned).

Poll et al.; U.S. Appl. No. 14/308,644 entitled "Sheath for hand-held and robotic laparoscopes," filed Jun. 18, 2014.

Farley et al.; Double-blind, prospective, randomized study of warmed, humidified carbon dioxide insufflation vs standard carbon dioxide for patients undergoing lararoscopic cholecystectomy; Arch Surg; 139; pp. 739-744; Jul. 2004.

Hashimoto et al.; Development of a fogless scope and its analysis using infrared radiation pyrometer; Surg Endosc; 11(8); pp. 805-808; Aug. 1997.

Ohdaira et al.; Antifogging effects of a socket-type device with the superhydrophilic, titanium dioxide coated glass for laparoscope; Surg endosc; 21(2); pp. 333-338; Dec. 2007.

Ott, Douglas E.; Chapter 1. Pneumoperitoneum: Production, management, effects and consequences; in Prevention & Management of Laparoendoscopic Surgical Complications, 1st Ed.; 6 pgs.; Jan. 1999 (retrieved from: http://laparoscopy.blogs.com/prevention_management/2006/02/chapter_1_pneum.html on Oct. 7, 2013).

Poll et al.; U.S. Appl. No. 14/733,752 entitled "View optimizer and stabilizer for use with surgical scopes," filed Jun. 8, 2015.

Poll et al.; U.S. Appl. No. 14/733,672 entitled "Device for maintaining visualization with surgical scopes," filed Jun. 8, 2015.

Drach et al.; U.S. Appl. No. 14/767,862 entitled "Fluid dispensing control systems and methods," filed Aug. 13, 2015.

Poll et al.; U.S. Appl. No. 15/385,693 entitled "Devices, systems, and methods for performing endoscopic surgical procedures," filed Dec. 20, 2016.

Poll et al.; U.S. Appl. No. 15/703,402 entitled "Sheath for hand-held and robotic laparoscopes," filed Sep. 13, 2017.

Poll et al.; U.S. Appl. No. 15/566,503 entitled "Endoscope having integrated visual field enhancement system," filed Oct. 13, 2017.

\* cited by examiner

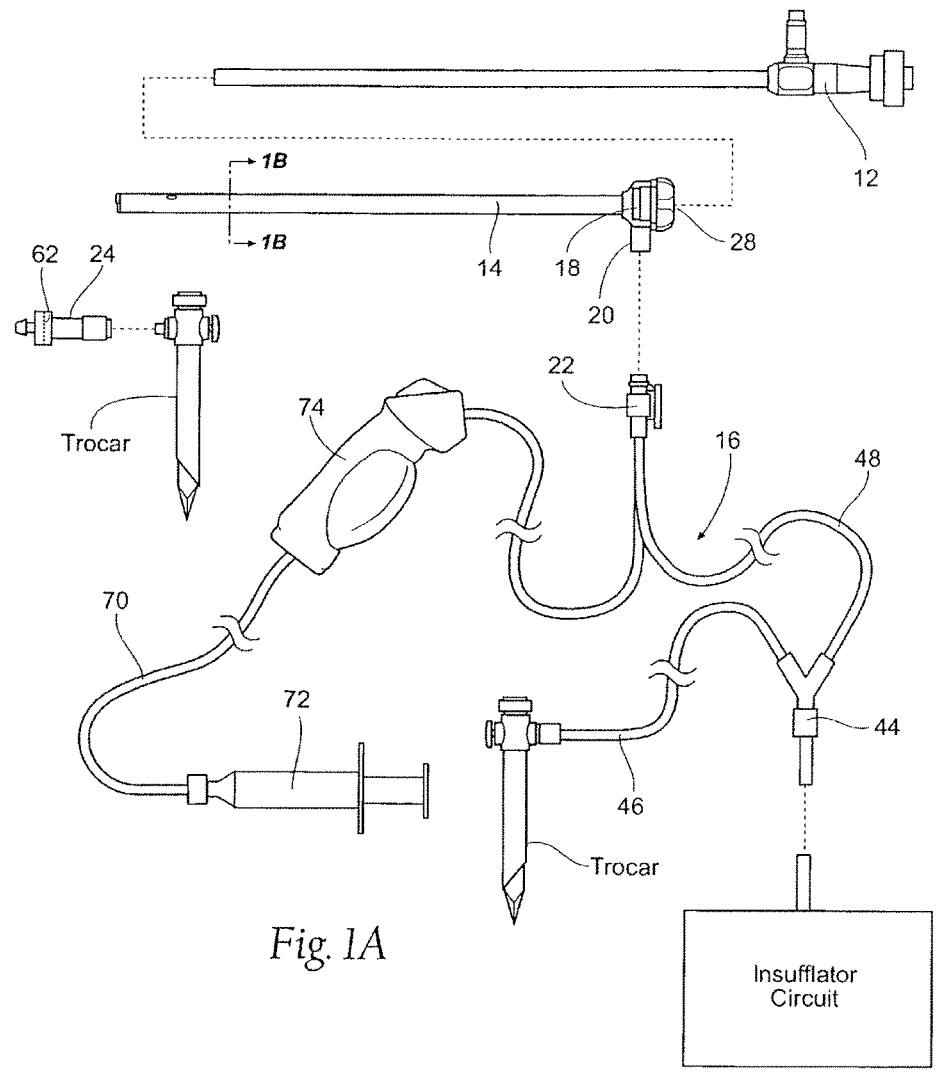
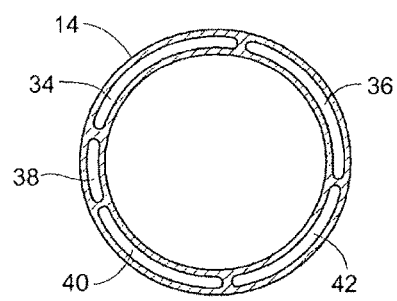
Fig. 1A
Fig. 1B

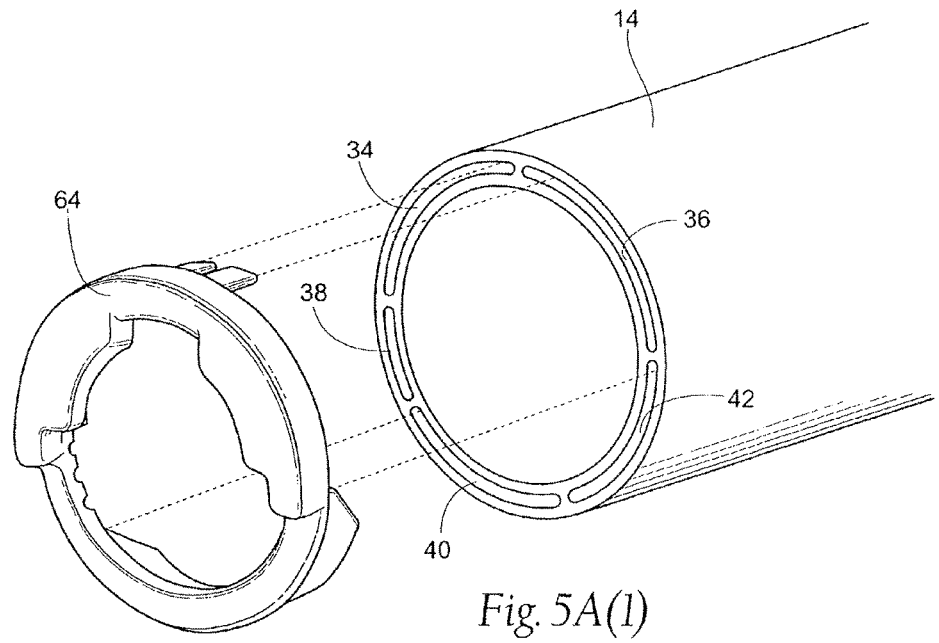
Fig. 5A(1)
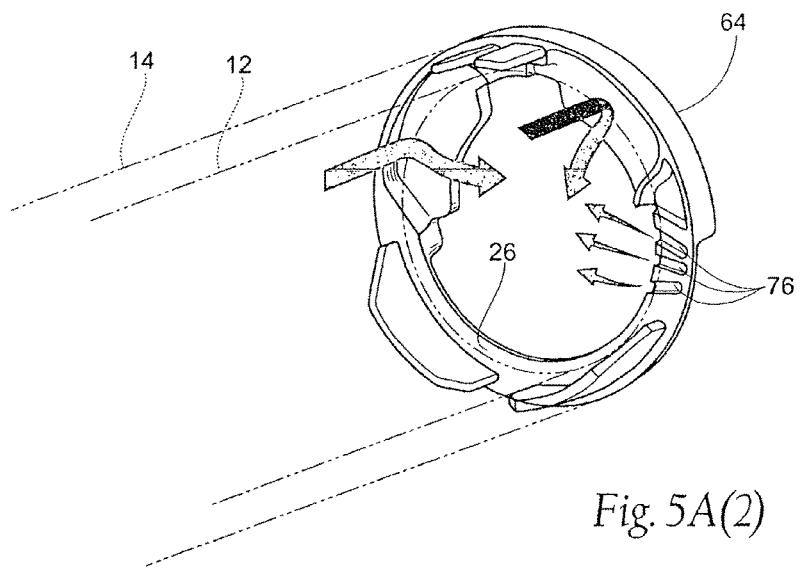
Fig. 5A(2)

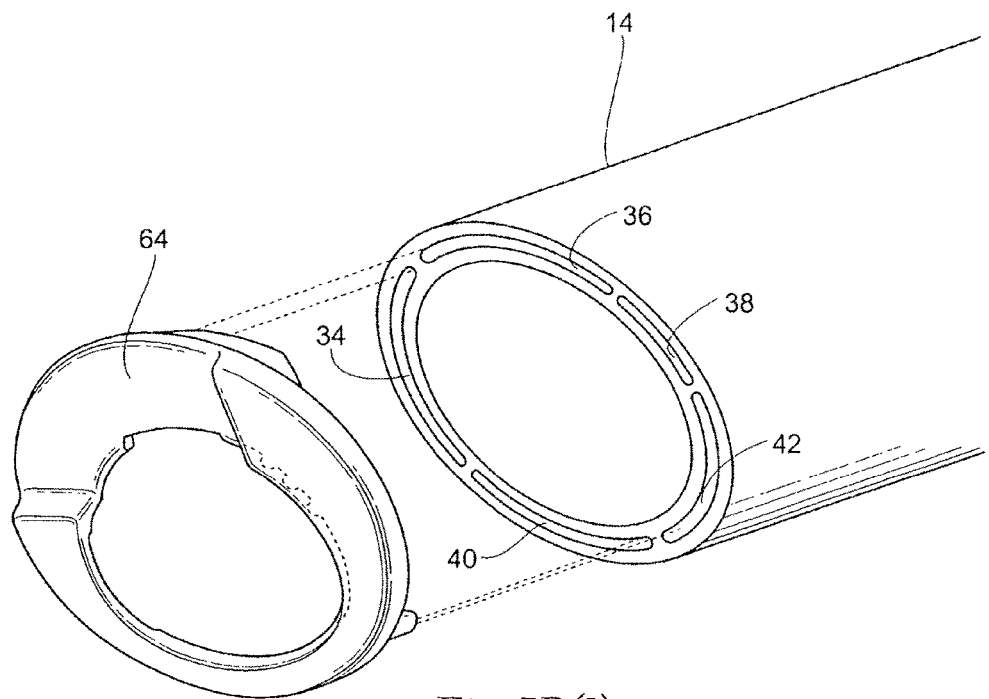
Fig. 5B(1)
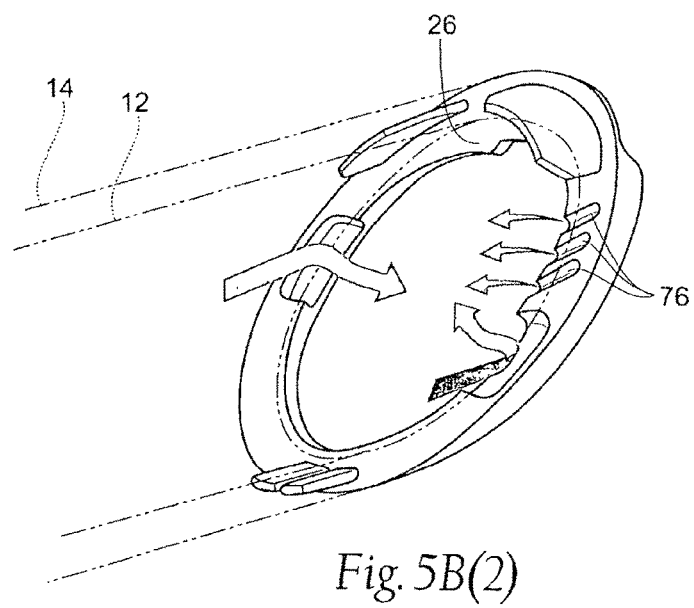
Fig. 5B(2)

SYSTEMS AND METHODS FOR OPTIMIZING AND MAINTAINING VISUALIZATION OF A SURGICAL FIELD DURING THE USE OF SURGICAL SCOPES

CROSS REFERENCE TO RELATED APPLICATIONS

This application is a continuation of U.S. patent application Ser. No. 12/653,148, filed on Dec. 9, 2009, titled "SYSTEMS AND METHODS FOR OPTIMIZING AND MAINTAINING VISUALIZATION OF A SURGICAL FIELD DURING THE USE OF SURGICAL SCOPES," now U.S. Patent Application Publication No. 2010-0198014-A1, which claims the benefit of U.S. Provisional Patent Application No. 61/121,514, filed Dec. 10, 2008, and titled "DEVICE FOR MAINTAINING VISUALIZATION WITH SURGICAL SCOPES," each of which is incorporated herein by reference.

U.S. patent application Ser. No. 12/653,148 also claims the benefit of U.S. Provisional Patent Application No. 61/170,864 filed Apr. 20, 2009, and titled "SURGICAL SCOPE STABILIZER FOR USE WITH DEVICE FOR MAINTAINING VISUALIZATION WITH SURGICAL SCOPES," which is also incorporated herein by reference.

U.S. patent application Ser. No. 12/653,148 is also a continuation-in-part of U.S. patent application Ser. No. 11/765,340, filed on Jun. 19, 2007, titled "DEVICE FOR MAINTAINING VISUALIZATION WITH SURGICAL SCOPES," now U.S. Patent Application Publication No. 2008-0319266-A1, which corresponds to International Application No. PCT/US2008/067426, filed Jun. 19, 2008, and titled "DEVICE FOR MAINTAINING VISUALIZATION WITH SURGICAL SCOPES," each of which is incorporated herein by reference.

FIELD

The invention generally relates to surgical scopes, and, more particularly, for optimizing and maintaining visualization of a surgical field when using a surgical scope, such as, e.g., a laparoscope.

BACKGROUND

Minimally invasive surgical procedures utilizing surgical scopes are desirable because they often provide one or more of the following advantages: reduced blood loss; reduced post-operative patient discomfort; shortened recovery and hospitalization time; smaller incisions; and reduced exposure of internal organs to possible contaminants.

Generally, minimally invasive surgeries utilize scopes, such as laparoscopes, that permit remote visualization of a surgical site within a patient's body while the surgical procedure is being performed. During a laparoscopic procedure, the patient's abdominal or pelvic cavity is accessed through two or more relatively small incisions rather than through a single large incision that is typical in a conventional surgery. Surgical scopes, such as laparoscopes, usually consist in part of a rigid or relatively rigid rod or shaft having an objective lens at one end and an eyepiece and/or integrated visual display at the other. The scope may also be connected to a remote visual display device or a video camera to record surgical procedures.

In laparoscopic surgeries, the abdomen is typically inflated with a gas through the use of an insufflator, to distend the abdominal space by elevating the abdominal wall above the internal organs and thereby create a sufficient working and viewing space for the surgeon. Carbon dioxide is usually used for insufflation, though other suitable gases may also be used. Conventional insufflators are adapted to cycle on and off to maintain a preset and suitable pressure within the patient's body cavity.

The local environment within a patient's abdominal space is generally rather warm and humid, and the use of devices such as harmonic scalpels and other cutting and coagulating devices generate mist, smoke, and other debris that is released into the surgical field and often becomes suspended throughout the expanded abdominal space. Additionally, blood, bodily fluids, pieces of tissue, fat or other bodily material may come in contact with or even attach to the lens. As a result of these conditions, visualization through the scope can be significantly diminished. Typically, the only solution to fogging and debris collection on the lens is removal of the scope from the body cavity and defogging or cleaning the lens by wiping it with a cloth, warming the scope tip, or utilizing another defogging method. The need to remove the scope to defog and remove debris from the lens is inconvenient for the scope operator and the surgeon and can interrupt and undesirably prolong surgical procedures.

SUMMARY OF THE DISCLOSURE

One aspect of the invention provides a view optimizing assembly having a deflector assembly with critical physical, pneumatic, and optical characteristics that make possible intra-operative defogging, surgical debris deflection, and cleaning of a laparoscope lens during minimally invasive surgery, while also maintaining visualization of the surgical site. In use, the view optimizing assembly makes possible the practice of a surgical method for maintaining clear visualization of the surgical site without removing the laparoscope 12 from the abdominal cavity for the purpose of cleaning or de-fogging its lens.

Another aspect of the invention provides a view optimizing assembly having a quick exchange feature. In use, the quick exchange feature makes possible a surgical method for maintaining clear visualization that includes the ability to make a quick exchange of laparoscopes having different operating characteristics (e.g., laparoscopes with different tip angles, lengths, or diameters) entirely on the sterile operating field and without interference with the preexisting surgical set-up on the sterile operating field. The view optimizing assembly integrates with the existing suite of minimally invasive instrumentation. It does not interfere with the surgical set-up, and it requires minimal change in the process or practice of a surgical operating room (OR) team.

BRIEF DESCRIPTION OF THE DRAWINGS

FIG. 1A is a somewhat schematic views of a view optimizing assembly for use with a laparoscope having a 0° shaft tip.

FIG. 1B is a section view of the sheath, showing internal fluid flow lumens, taken generally along line 1B-1B in FIG. 1A.

FIGS. 5A(1) and 5A(2) are enlarged, exploded views of the deflector assembly for use with a laparoscope having a 0° shaft tip.

FIGS. 5B(1) and 5B(2) are enlarged, exploded views of the deflector assembly for use with a laparoscope having an angled shaft tip.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. View Optimizing Assembly

A. Overview

Figure 2A:
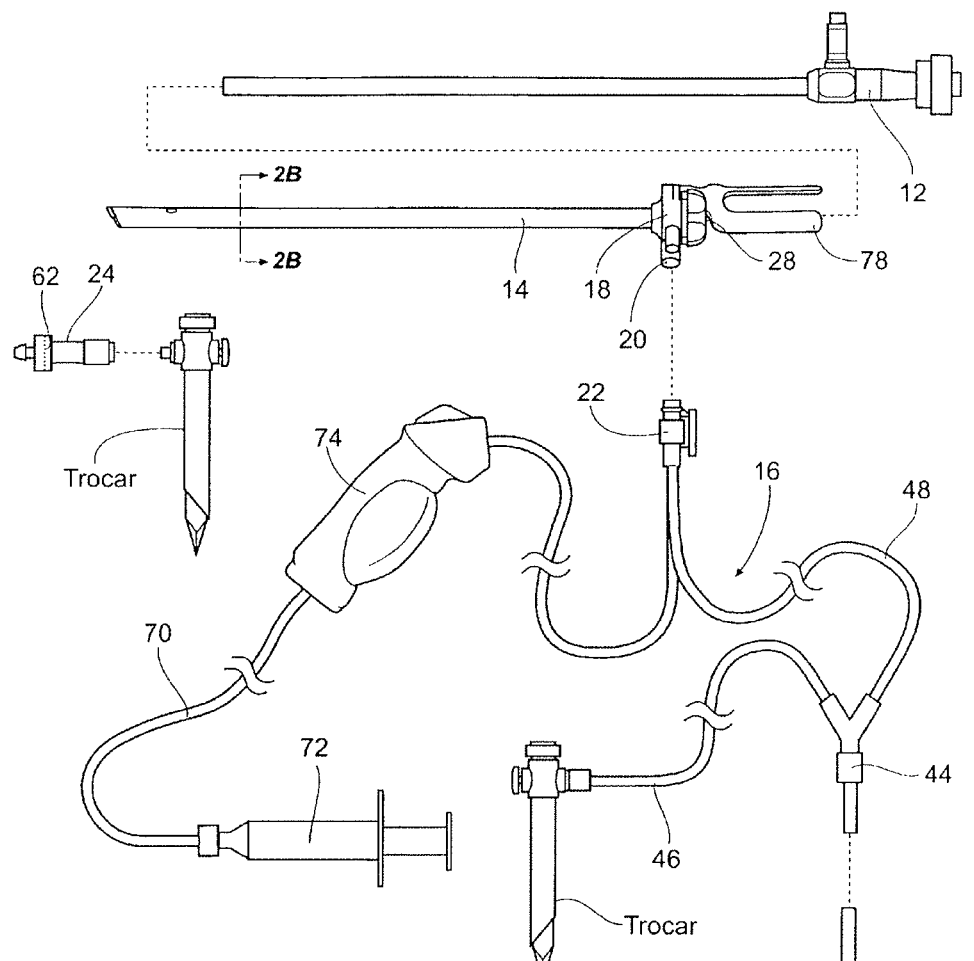
FIG. 2A is a somewhat schematic of a view optimizing assembly for use with a laparoscope having an angled shaft tip.

FIGS. 1A/1B and FIG. 2A/2B show a view optimizing assembly 10 for use in association with a state of the art laparoscope 12. In FIGS. 1A/1B, the laparoscope 12 possesses a 0° (blunt) shaft tip. In FIGS. 2A/2B, the laparoscope possess an angled shaft tip (e.g., a 30° shaft tip or 45° shaft tip). The components of the view optimizing assembly 10 may be made from plastic materials (extruded and/or molded), but other suitable materials, such as metal or a composite material, or combinations thereof could be used.

As will be described in greater detail, the view optimizing assembly 10 facilitates intra-operative defogging, surgical debris deflection, and cleaning of a laparoscope lens during minimally invasive surgery, while also maintaining visualization of the surgical site. The view optimizing assembly 10 is intended to be a single-use, disposable laparoscopic accessory. The view optimizing assembly 10 is desirably a sterile accessory for immediate set up and use on a sterile operating field.

As shown in FIGS. 1A and 2A, the view optimizing assembly 10 comprises a multi-lumen sheath assembly 14, which mounts over the shaft of the laparoscope 12. The end of the shaft is sized and configured to match the size and configuration of the corresponding laparoscope 12, having a blunt tip in FIG. 1A and angled tip in FIG. 2A. The assembly 10 includes a tubing set 16 to connect the sheath 14 to an existing anhydrous carbon dioxide ($CO_2$) insufflation circuit.

In use, the view optimizing assembly 10 makes possible the practice of a surgical method for maintaining clear visualization of the surgical site without removing the laparoscope 12 from the abdominal cavity for the purpose of cleaning or de-fogging its lens. Furthermore, the view optimizing assembly 10 also makes possible a surgical method for maintaining clear visualization that includes the ability to make a quick exchange of laparoscopes having different operating characteristics (e.g., laparoscopes with different tip angles, lengths, or diameters) entirely on the sterile operating field and without interference with the preexisting surgical set-up on the sterile operating field. The view optimizing assembly 10 integrates with the existing suite of minimally invasive instrumentation. It does not interfere with the surgical set-up, and it requires minimal change in the process or practice of a surgical operating room (OR) team.

Figure 7:
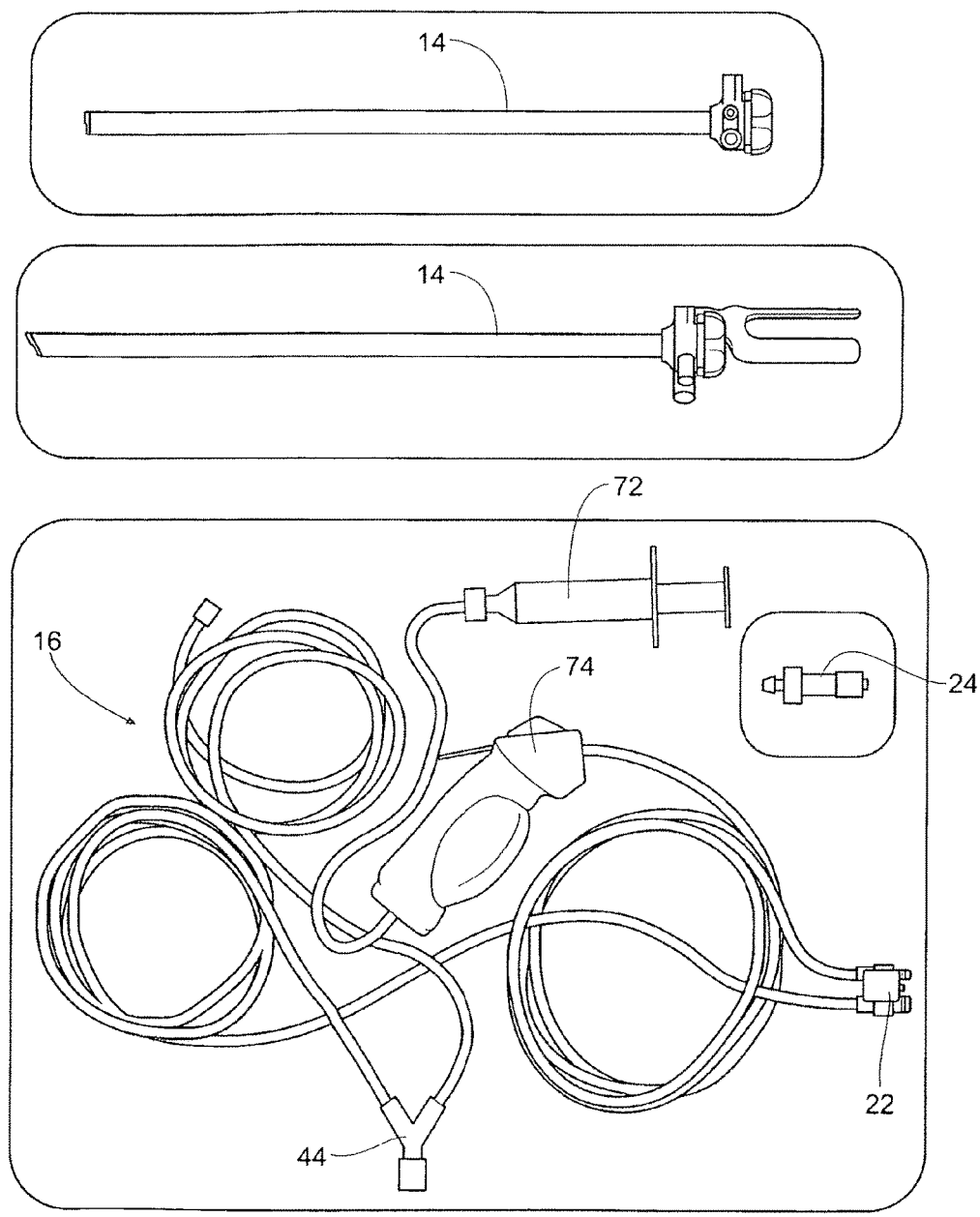
FIGS. 7 to 34 illustrate a representative method including the set up and use of the view optimizing assembly using sterile technique by technicians/operating room personnel.

The view optimization assembly 10 desirably comes packaged for use in sterile peel away pouches (see FIG. 7). As also shown in FIGS. 1A and 2A, the pouches contain the components of the view optimization assembly 10, including the sheath 14 and a manifold 18 that is assembled to the sheath 14 and that includes a quick exchange coupling 20; the tubing set 16 which includes a quick exchange coupler 22 that mates with the quick exchange coupling 20 on the manifold 18; and (optionally) a vent device 24.

B. The Sheath/Manifold Assembly

As shown in FIGS. 1A and 2A, the sheath 14/manifold 18 assembly includes a sheath 14 that is sized and configured to receive a laparoscope 12 having a prescribed tip angle, length, and diameter. The sheath 14 includes a stop 26 (see FIGS. 5A(2) and 5B(2)) formed adjacent the distal end of the sheath 14. The stop 26 prevents advancement of the laparoscope 12 beyond the distal end of the sheath 14, so that lens at the distal end of the laparoscope 12 rests in a desired, generally coterminous alignment with the distal end of the sheath 14. The sheath 14 also includes a locking collar 28 at its proximal end to frictionally engage the laparoscope 12 and resist axial withdrawal of the laparoscope 12 from the sheath 14.

Figure 14:
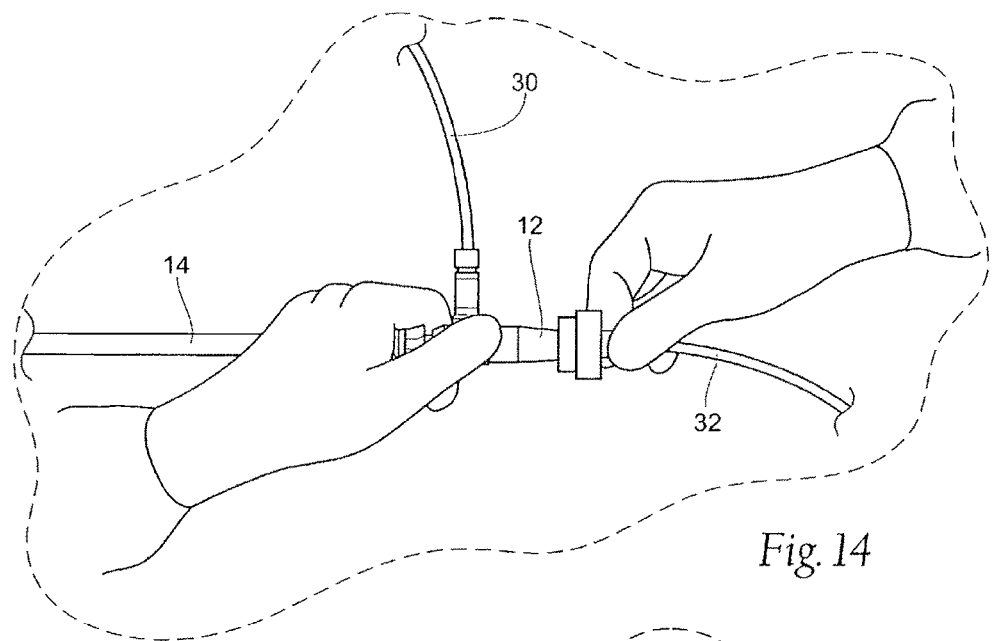

In use, it is expected that the laparoscope 12 will be inserted into the sheath 14 by a scrub nurse during set-up for the operation (see FIGS. 8 to 11). The assembled laparoscopic and sheath 14 will then be handed as a unit to personnel at the operating room (OR) table at the desired time). The laparoscope 12 is then connected by personnel at the OR table in conventional fashion to a light cable 30 (which directs light to illuminate the operative field) and the camera cable 32 (which takes the image from the scope and displays it on monitors in the OR) (see FIG. 14). The sheath 14 is sized and configured not to interfere with this normal set-up of the laparoscope 12.

Figure 16:
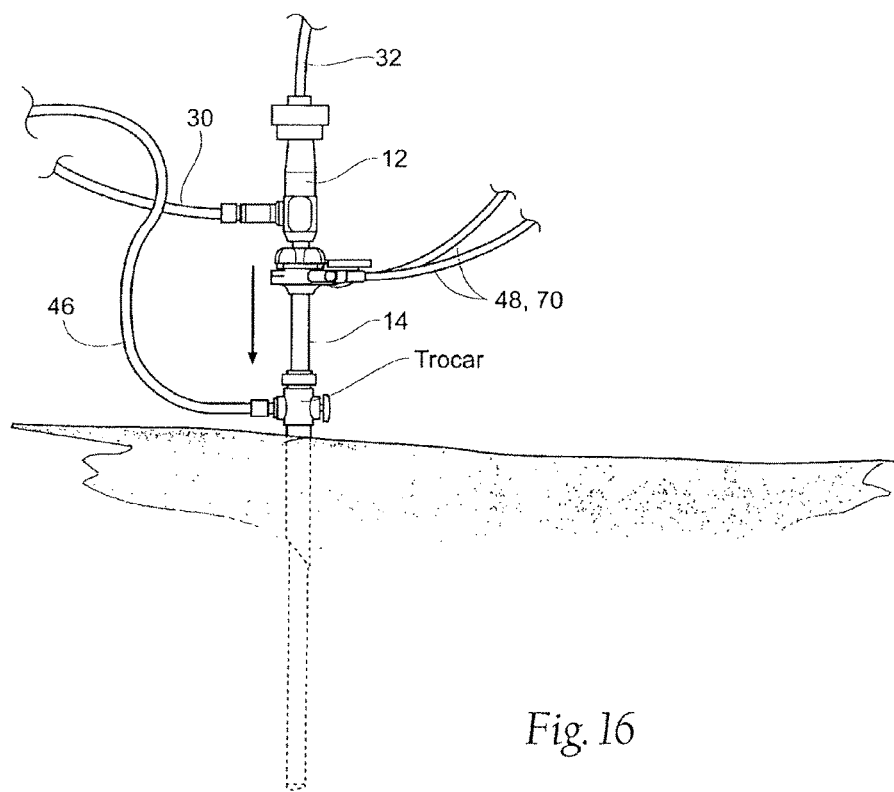

In use, the assembled laparoscopic and sheath 14 are placed as a unit through a trocar into the body cavity (e.g., the abdominal cavity), for viewing the surgical procedure as it is performed (see FIG. 16).

Figure 2B:
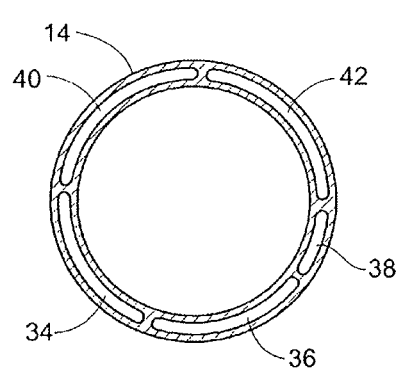
FIG. 2B is a section view of the sheath, showing internal fluid flow lumens, taken generally along line 2B-2B in FIG. 2A.
Figure 3A:
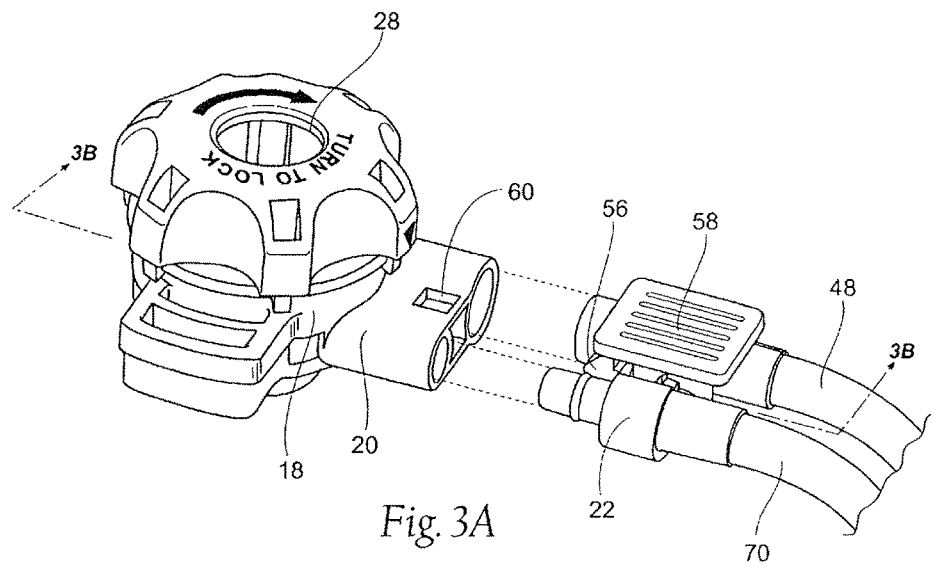
FIG. 3A is an enlarged perspective view of a manifold that the view optimizing assembly shown in FIG. 1A or FIG. 2A incorporates, including a quick exchange coupling, and a quick exchange coupler that the tubing set shown in FIG. 1A or FIG. 2A incorporates, the coupling and the coupler being disconnected.

As shown in FIGS. 1A and 2A, and as further shown in FIG. 3A, the sheath 14/manifold 18 assembly also includes the manifold 18 at the proximal end of the sheath 14. The manifold 18 communicates with multiple lumens (five, 34 to 42, are shown in the illustrated embodiment) formed within the wall of the sheath 14 (see FIGS. 1B and 2B). In use, the lumens 34 to 42 convey anhydrous $CO_2$ to the distal end of the sheath 14; vent or exhaust air from the distal end of the sheath 14 through the manifold 18; and, if desired, convey sterile fluid and bursts of air to the distal end of the sheath 14. In a representative embodiment (see FIGS. 1B and 2B), two lumens 34 and 36 are dedicated to the transport of $CO_2$; two lumens 40 and 42 are dedicated to venting; and one lumen 38 is dedicated to the transports of sterile fluid or air.

C. The Tubing Set

As previously described, the tubing set 16 includes a quick exchange coupler 22 that mates with the quick exchange coupling 20 on the manifold 18 (see FIGS. 3A/3B and 4A/4B). The tubing set 16 includes lengths of flexible medical grade tubing with individual end couplers (best shown in FIGS. 1A and 2A) that connect to an existing $CO_2$ insufflation circuit and, if desired, a source of sterile fluid (saline or sterile water, preferably with a "surface active agent") on the sterile operating field (e.g., a bag or a syringe). The tubing set 16 includes a Y-connector 44 that divides the anhydrous $CO_2$ output of the insufflation circuit in a first branch 46 for coupling to an insufflation trocar inserted in the body cavity (as will be described later), and a second branch 48 coupled to the quick exchange coupler 22.

The second branch 48 diverts a small portion of the $CO_2$ output (e.g., 20% or less) to the quick exchange coupler 22.

Figure 3B:
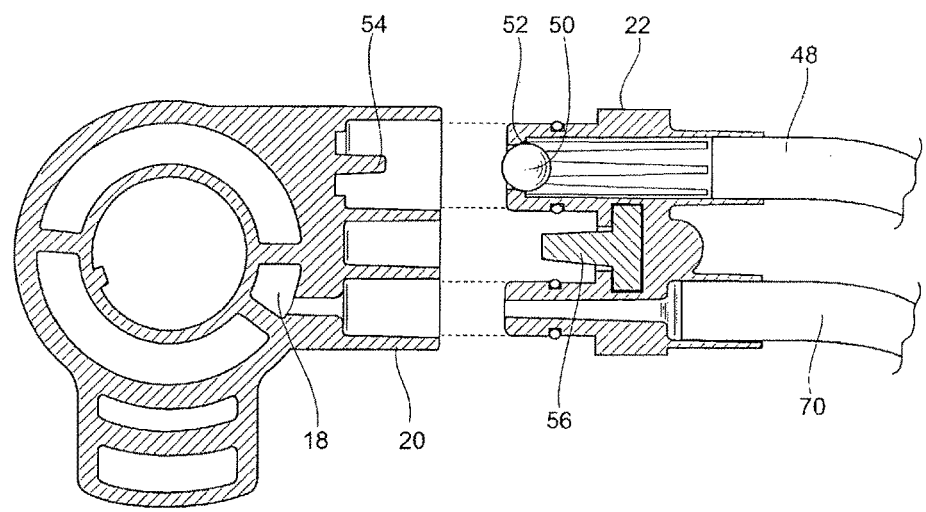
FIG. 3B is a sectional view taken generally along line 3B-3B in FIG. 3A, showing a one way check valve that is normally closed.
Figure 4A:
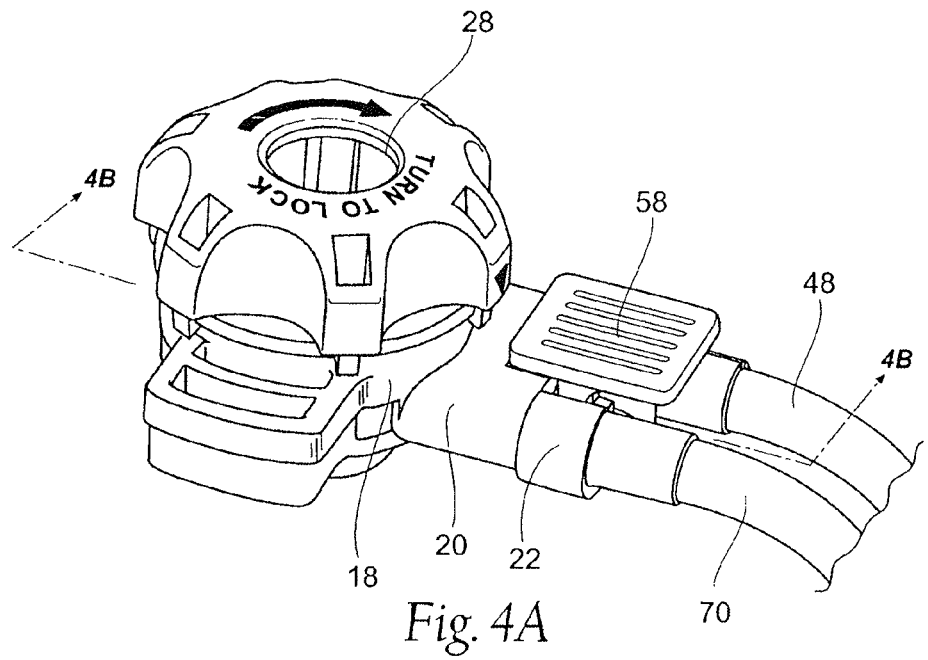
FIG. 4A is an enlarged perspective view of the manifold including a quick exchange coupling and the quick exchange coupler of the tubing set, as shown in FIG. 3A, but now connected.
Figure 4B:
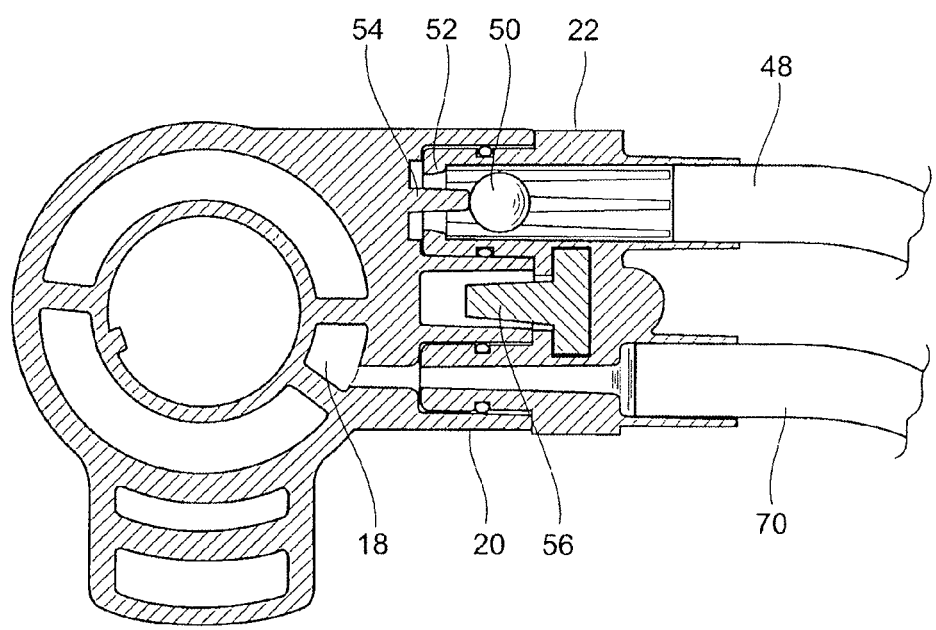
FIG. 4B is a sectional view taken generally along line 4B-4B in FIG. 4A, showing the one way check valve that is opened by the connection of the quick exchange coupling and connectors.

As shown in FIGS. 3B and 4B, the quick exchange coupler 22 includes a one way check valve 50 that communicates with the second branch 48 of the tubing set 16. In the illustrated embodiment, the check valve 50 comprises a ball valve. Insufflation pressure normally presses the ball valve 50 against a ball valve seat 52 (as shown in FIG. 3B). A projection 54 in the manifold 18 displaces the ball valve 50 from the valve seat 52 when the quick exchange coupler 22 mates with the quick exchange coupling 20 on the manifold 18 (as shown in FIG. 4B). Unseating the ball valve 50 opens flow communication through the check valve 50. In the absence of coupling the quick exchange coupler 22 on the tubing set 16 to the quick exchange coupling 20 on the manifold 18, the check valve 50 remains closed, normally blocking flow of $CO_2$ through the second branch 48.

Thus, the tubing set 16 accommodates the set-up of the supply of the entire $CO_2$ output to a insufflation trocar through the tubing set 16, separate and independent of the connection of the tubing set 16 to the manifold 18 of the sheath 14.

As FIGS. 3A and 4A further show, a latch 56 carried on a spring-biased button 58 on the quick exchange coupler 22 "clicks" into a detent 60 on the quick exchange coupling 20 on the manifold 18 to reliably lock the coupler 22 and coupling 20 together for use, opening the check valve to flow $CO_2$ through the second branch 48 (shown in FIGS. 4A/4B). Depressing the button 58 allows the quick exchange coupler 22 and coupling 20 to be separated, and the check valve 50 will close in response to insufflation pressure in the second branch 48 (as shown in FIGS. 3A/3B).

Figure 15:
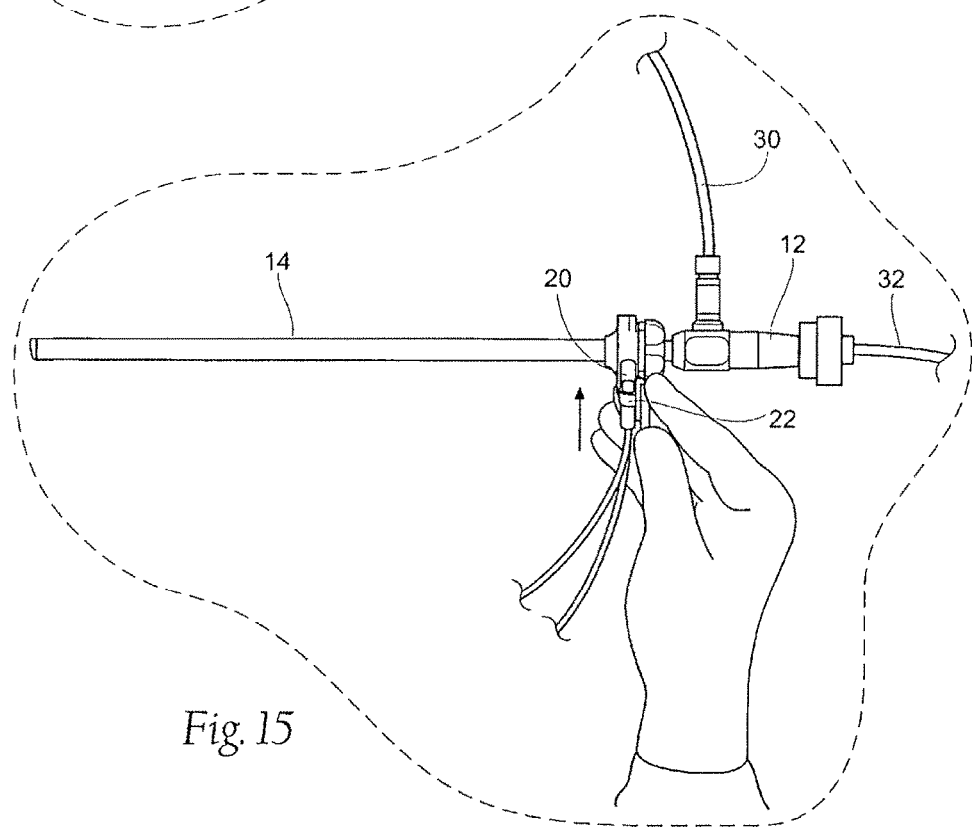
Figure 22:
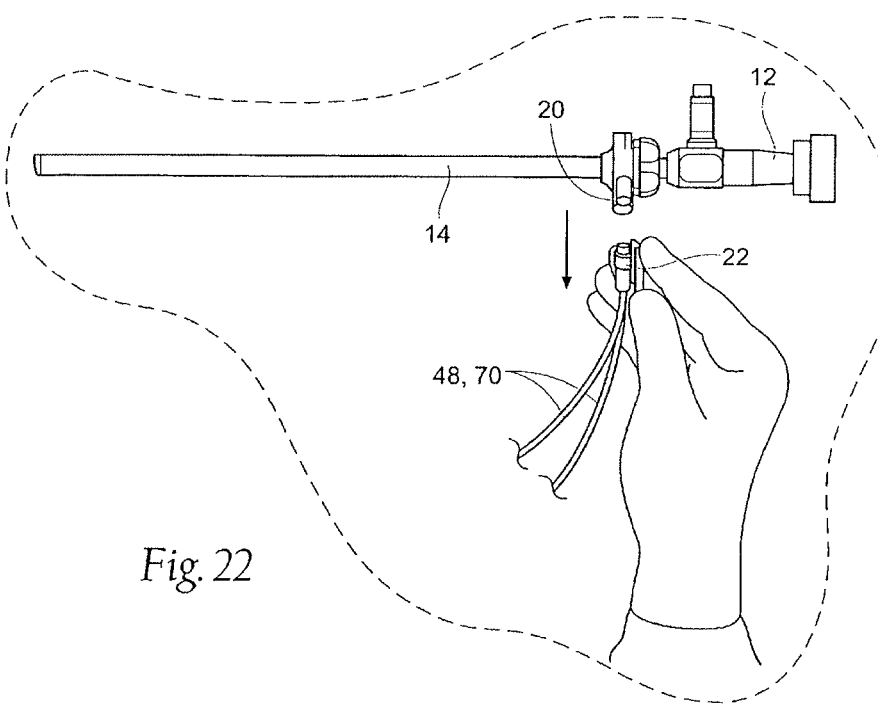
Figure 23:
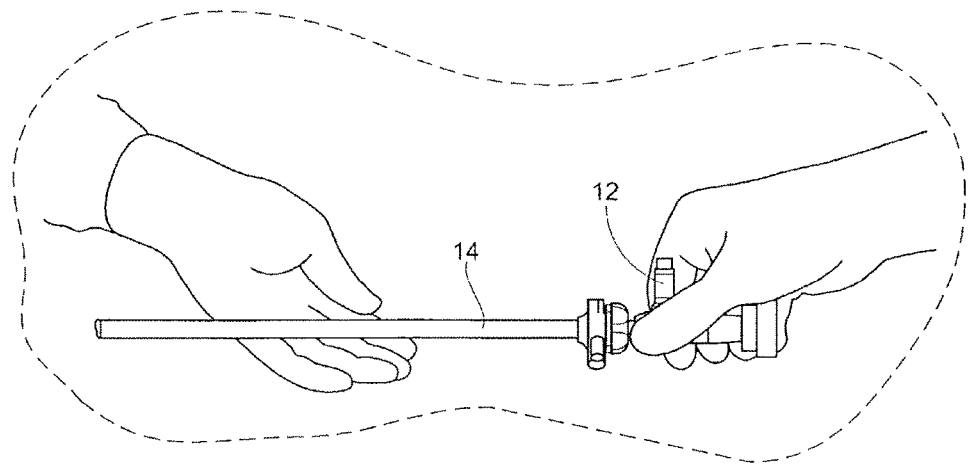
Figure 24:
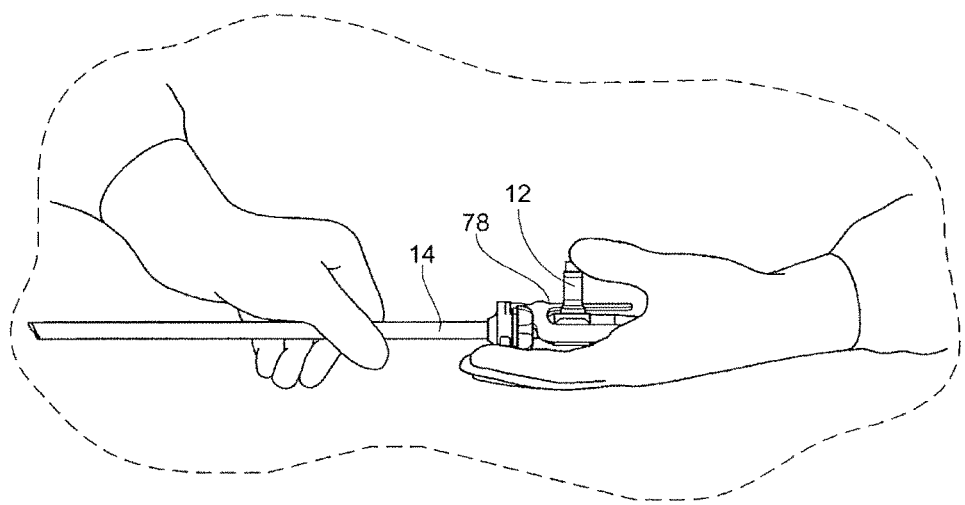
Figure 25:
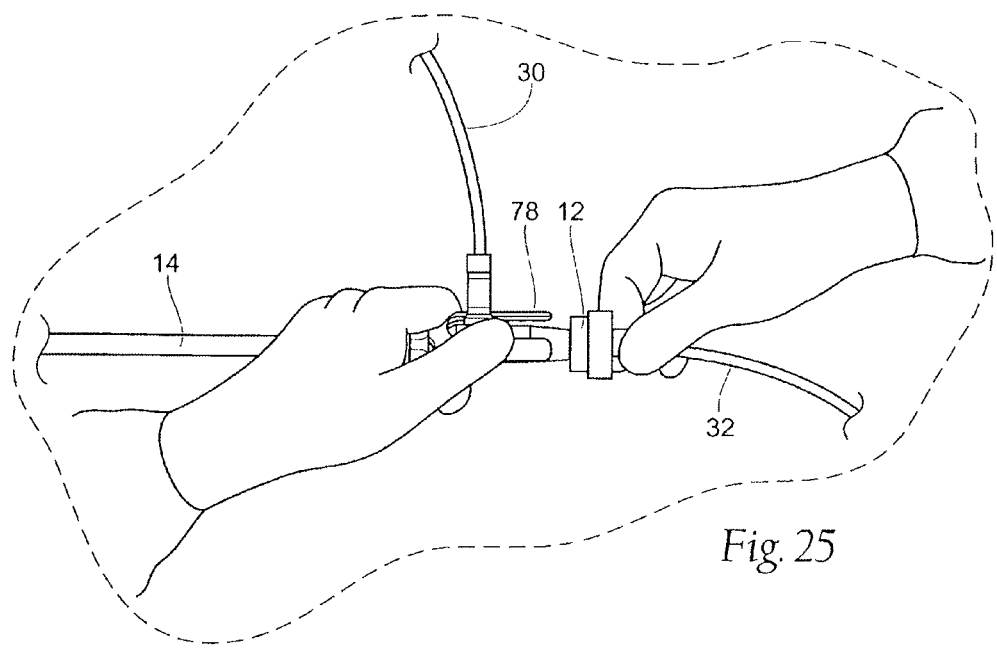
Figure 26:
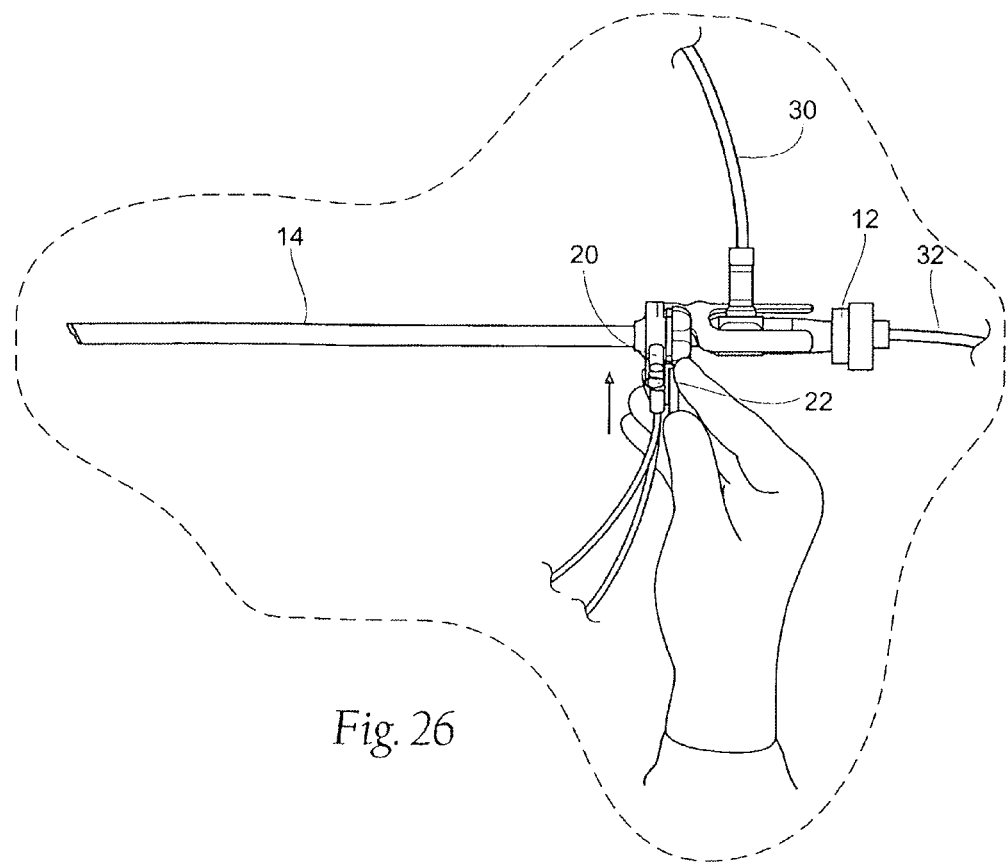
Figure 27:
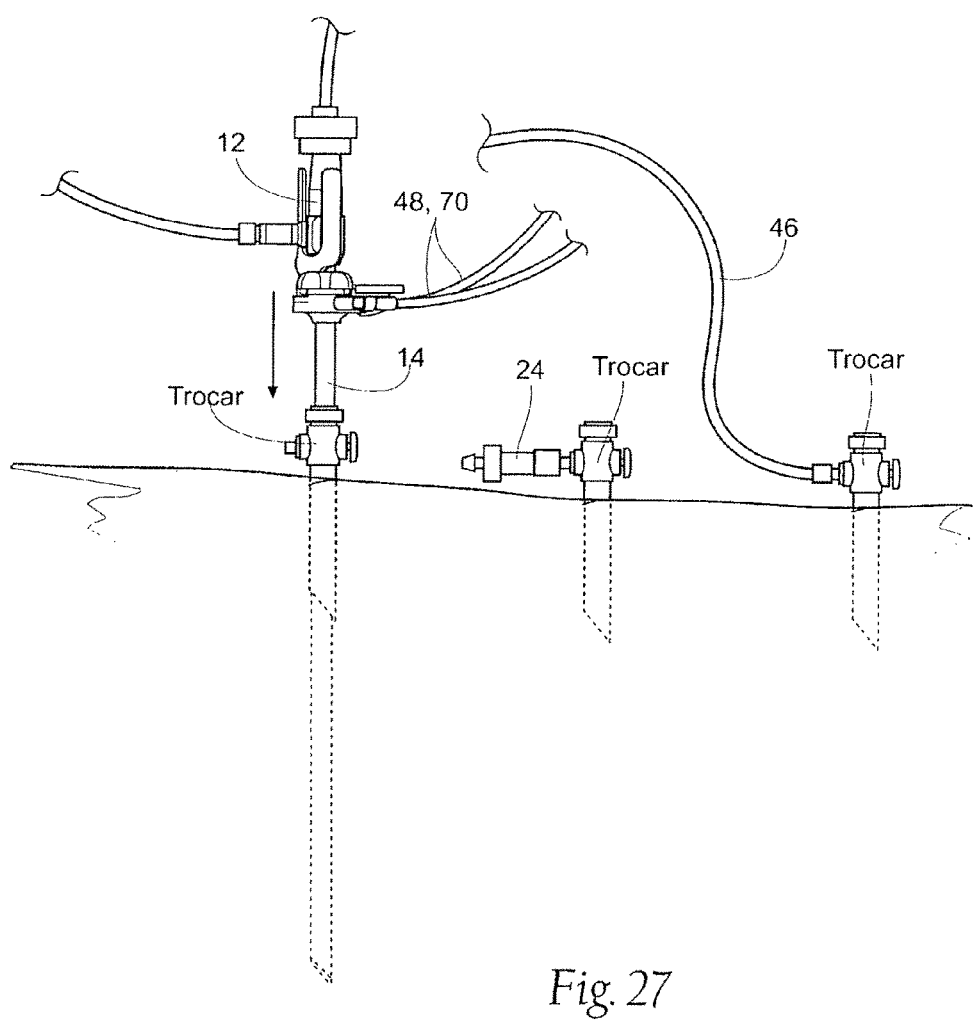

Connection of the quick exchange coupling 20 on the manifold 18 to the quick exchange coupler 22 on the tubing set 16 is intended to occur at the OR table in the normal course, after the laparoscope 12 is connected to the light cable 30 and the camera cable 32 (see FIG. 15). Upon coupling, the one way check valve 50 is opened, and the manifold 18 directs the small portion of $CO_2$ from the $CO_2$ insufflation circuit. Disconnection of the of the quick exchange coupling 20 on the manifold 18 to the quick exchange coupler 22 on the tubing set 16 is also intended to occur at the OR table in the normal course, after a removal and/or exchange of a laparoscope 12 (see FIG. 22).

D. The Vent Device

The vent device 24 (see FIGS. 1A and 2A) comprises a tube with an inline membrane 62 that restricts air flow through the tube. A proximal end of the tube is sized and configured to couple to a stopcock valve of a conventional trocar, as will be described later. In use, the vent device 24 provides a controlled leak of $CO_2$ from the operating cavity, as will also be described in greater detail later.

E. The Deflector Assembly

1. $CO_2$

The sheath 14 includes at its distal end a deflector assembly 64 (see FIGS. 5A(1) and 5A(2) for a blunt shaft tip and FIGS. 5B(1) and 5B(2) for an angled shaft tip). The deflector assembly 64 projects a predetermined distance beyond the distal end of the sheath 14, and thus also a predetermined distance beyond the lens at the distal end of the laparoscope 12. The deflector assembly 64 communicates with the lumens in the sheath 14. The deflector assembly 64 is sized and configured to direct the small portion of the $CO_2$ from the insufflation circuit in a prescribed flow path and flow velocity continuously across the laparoscopic lens.

The desired flow path and flow velocity of $CO_2$ established by the deflector assembly 64 continuously across the laparoscopic lens creates a "wind shear." The wind shear path of anhydrous $CO_2$ prevents fogging. The desired flow path and flow velocity of $CO_2$ established by the deflector assembly 64 continuously across the laparoscopic lens also desirably serves to deflect smoke and surgical debris away from the laparoscopic lens during surgery.

2. Physical, Pneumatic, and Optical Characteristics of the Deflector Assembly

The size and configuration of the deflector assembly are defined and constrained by several, sometime overlapping considerations including (i) prescribed physical characteristics, which are imposed due to the need to access the operating environment in as minimally invasive manner as possible and to be compatible with state of the art laparoscopes and other laparoscopic surgical instruments and techniques; (ii) prescribed pneumatic characteristics, which are imposed due to the need to create a particular "wind shear" effect in terms of the flow path and flow velocity of $CO_2$ across the laparoscopic lens; and (iii) prescribed optical characteristics, which are imposed due to the need to prevent interference with the field of view and the visualization of the operating field by the laparoscope 12.

3. Physical Characteristics

The size and configuration requirements for minimally invasive access compatible with state of the art laparoscopic instrumentation and techniques are paramount. These requirements impose constrains upon the minimum inside diameter of the sheath 14 as well as the maximum outside diameter of the sheath 14. Because state of the art laparoscopes are provided with different shaft diameters, lengths, and lens configurations, the sheath dimensions and configuration change for compatibility with them. The view optimizing assembly 10 actually includes a family of sheath 14/manifold 18 assemblies differently sized and configured to accommodate different classes of laparoscopes, to make possible compatibility with the families of state of the art laparoscopes that are in use.

For example, state of the art laparoscopes include 10 mm laparoscopes, 5 mm laparoscopes, and, within these sizes, 0° shaft tips, 30° shaft tips, and 45° shaft tips. Further, within these classes of laparoscopes, manufacturing tolerances typically vary from scope to scope, as well as from manufacturer to manufacturer. A given sheath 14/manifold 18 assembly for a given laparoscope class (e.g., 10 mm or 5 mm) desirably takes these typical manufacturing and manufacturer variances into account, and is desirably sized and configured to fit the largest scope variance encountered within a given laparoscope class.

To maximize the fluid flow lumen area within the sheath 14, the minimum inside diameter of a given sheath 14 must closely conform to the maximum outside diameter of the shaft of the particular state of the class of laparoscope 12 selected for use, which the sheath 14 must accommodate in a smooth, sliding fit. Further, a gap between the outside diameter of the laparoscope shaft and the inside diameter of the sheath 14 must be minimized to avoid the transport and leakage of blood and fluids from the operating field. Still further, minimizing the gap also assures that the laparoscope 12 self-centers in the sheath 14, thereby assuring faithful and accurate visualization through the laparoscope lens.

For example, for a typical laparoscope 12 in the 10 mm class, which measures 0.392 inch, the inside diameter of the sheath 14 is manufactured to 0.405 inch, providing a gap thickness of 0.0064 inch. For a 5 mm laparoscope 12 in the 5 mm class, which measures 0.196 inch, the inside diameter of the sheath 14 is manufactured to 0.218 inch, providing gap thickness of 0.011 inch.

The maximum outside diameter of the sheath 14 for minimally invasive access must take into account the minimum inside diameter of the trocar, which the maximum outside diameter cannot exceed.

For example, for a typical 10 mm trocar that measures 0.509 inch, the outside diameter of the sheath 14 is manufactured to 0.486 inch, providing a gap thickness of 0.0115 inch. For a typical 5 mm trocar that measures 0.324 inch, the outside diameter of the sheath 14 is manufactured to 0.300 inch, providing a gap thickness of 0.012 inch.

It is desirable, given the particular size and configuration constraints of the laparoscopic instrumentation and techniques used, to maximize the outside diameter to the extent possible. This is because, together the inside and outside diameters of the sheath 14 define the wall thickness for the sheath $S_w$. The wall thickness $S_w$, together with the length of the sheath 14, in turn, define the maximum area available for the transport of the $CO_2$ and fluids by the sheath 14. The area of the fluid flow lumen or lumens dedicated to the supply of $CO_2$, in turn, defines the maximum flow rate of the $CO_2$ directed by the deflector assembly 64. The flow rate should be sufficient at a minimum, given the output of the insufflator selected for use, to supply anhydrous $CO_2$ across the lens of the laparoscope 12 sufficient to prevent fogging. Also affecting the effectiveness of the $CO_2$ to defog the lens, is the water content of the anhydrous $CO_2$. Given the same flow rate, the less water that is present in the anhydrous $CO_2$, the greater is the defogging capacity of the assembly. Further, the flow rate desirable should also be sufficient to deflect smoke and surgical debris away from the viewing field of the laparoscopic lens during surgery, so that the anhydrous $CO_2$ directed by the deflector assembly 64 both defogs and deflects debris.

Medical grade $CO_2$ for use with conventional insufflators is typically 99% pure, that is, no more than 1% of the gas is other than $CO_2$, and such medical grade anhydrous $CO_2$ generally has a maximum moisture content of 25 parts per million by volume. Typically, a state of the art insufflator circuit delivers anhydrous $CO_2$ at a max flow rate of about 20 liters per hour. Typically, the insufflator circuit will sense pressure in the circuit and cycle off when the sensed pressure is at or above 15 mmHg and cycle on when the sensed pressure is below 15 mmHg.

Given the above sheath dimensions, and given the supply of typical medical grade anhydrous $CO_2$, a flow rate of at least about 1.0 liters per minute is critical to achieving this objective. Given the above dimensions, and the supply of typical medical grade anhydrous $CO_2$, a flow rate less than 0.8 liters per minute is not sufficient to prevent significant accumulation of moisture on the laparoscope lens.

In a representative embodiment, for a sheath 14 having an inside diameter of 0.405 inch and an outside diameter of 0.486 inch, and a length of 11.25 inch (which accommodates passage of a typical 10 mm laparoscope and its own passage through a conventional trocar) (i.e., $S_w$=0.081 inch), the total area available in the sheath wall is 0.056 square inches. Based upon required structural support within the wall (inside, outside, and radial) the total available area for lumens to transport fluids is 0.027 square inch.

In a representative embodiment, the total lumen area is occupied by five lumens 34 to 42, two for transporting $CO_2$ (34 and 36), one for sterile fluid (38), and two for passive exhaust air venting (40 and 42).

The area of each lumen can be maximized by selection of lumen geometry. In a representative embodiment, lumen geometry is generally triangular or pie shaped with rounded corners. The radial walls that separate the lumens within the sheath 14 are sized to minimize the spacing between the lumens.

In a representative embodiment, $CO_2$ transport is accomplished by two lumens 34 and 36 that extend about 175 degrees about the outer circumference of the sheath 14 and comprising a flow area of 0.013 square inches. Sterile fluid transport is accomplished by one lumen 38 comprising a flow area of 0.003 square inches. Exhaust air venting is accomplished by two lumens 40 and 42 comprising a flow area of 0.011 square inches. The distal openings of the exhaust lumens 40 and 42 desirably are spaced from the distal end of the sheath, to prevent uptake of blood and fluids.

4. Pneumatic Characteristics.

Figure 6:
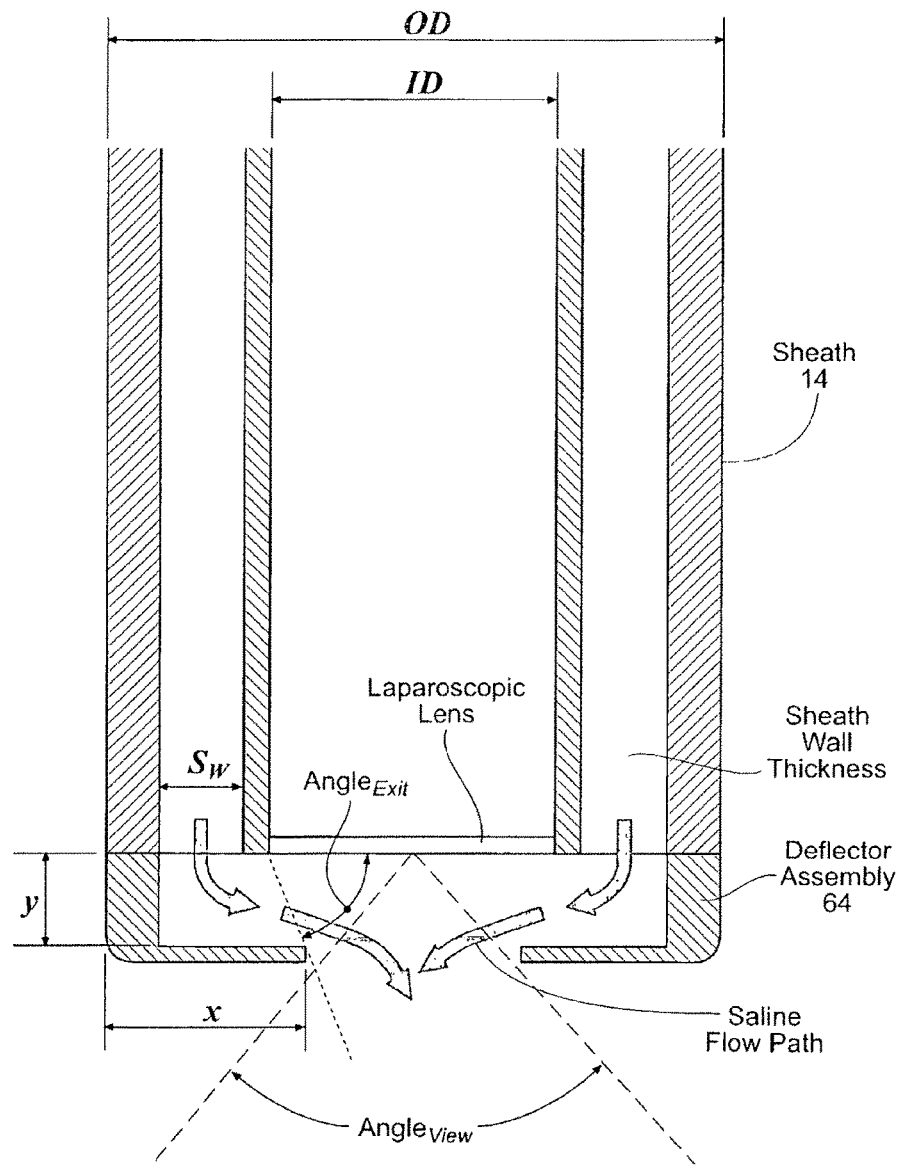
FIG. 6 is a schematic view of the critical physical, pneumatic, and optical characteristics of the deflector assembly shown in FIGS. 5A and 5B.

As diagrammatically shown in FIG. 6, the deflector assembly 64 must overhang the laparoscopic lens by a prescribed transverse distance, defining a deflection width X, sufficient to change the direction of $CO_2$ flowing axially through lumens of the sheath 14 (i.e., along the axis of the laparoscope shaft) into a non-axially, transverse path across the laparoscopic lens (i.e., at an angle relative to the axis of the laparoscope shaft). Still, the distance of the deflection width X should not extend to the point that is obstructs the field of the view of the laparoscopic lens. This is an example where a pneumatic characteristic of the deflector assembly 64 overlaps with an optical characteristic. Further optical characteristics will be described in greater detail below.

The deflector assembly 64 must also project axially beyond the distal terminus of the sheath 14 by a prescribed axial distance, defining an air channel distance Y, sufficient to maintain the $CO_2$ flowing along the path bounded by the deflection width X at a distance sufficiently close (proximal) to the laparoscopic lens to achieve the desired shear flow effect, but without forming an abrupt flow bend that can lead to a reduction in the desired $CO_2$ flow velocity.

Together, the deflection width X and the channel distance Y define the pneumatic characteristics of the deflection assembly. At the desired minimum flow rate, the pneumatic characteristics create a flow path that conveys $CO_2$ continuously across the laparoscopic lens at the desired flow velocity, in shorthand called the "wind shear." The pneumatic characteristics of the $CO_2$ "wind shear" across the laparoscopic lens prevent fogging, as well as desirably deflect smoke and surgical debris away from the viewing field of the laparoscopic lens during surgery.

Together, the pneumatic characteristics defined by the deflection width X and the channel distance Y create an exit angle $A_{EXIT}$, measured between the plane of the laparoscopic lens and the terminal edge of the deflector assembly 64. The exit angle $A_{EXIT}$ must be less than a maximum angle of 45 degrees, else the flow path of the $CO_2$ will not pass sufficiently both across and proximal to the laparoscopic lens. To maintain a desired exit angle $A_{EXIT}$, the channel distance Y should be at least equal to the wall thickness of the sheath $S_w$ and should not exceed 1.5 times the wall thickness of the sheath $S_w$. The deflection width X should be at least equally to two times the channel distance Y, but not extend into the field of view of the laparoscopic lens.

5. Optical Characteristics

The optical characteristics of the deflector assembly 64 are selected (i) to not block or reduce the illuminated image of the operating field provided by the laparoscope 12; (ii) not decrease the intensity of the illumination provided by the laparoscope 12 on the operating field; and (iii) prevent reflection of illumination light at the lens of the laparoscope 12.

As discussed above, the maximum deflection width X takes into account one of the desirable optical characteristics; namely, the deflection width X should not obstruct the field of the view of the laparoscopic lens.

To prevent the decrease of the illumination, the deflector assembly 64 is desirably made from a material having high light transmission properties (i.e., transparency), to not interfere with the passage of light through the light cable 30 onto the operating field as well as the passage of the reflected image conveyed to the camera cable 32 of the laparoscope 12.

Furthermore, the material and surface finish of the deflector assembly 64 must pose minimal reflectively to light. In a representative embodiment, the deflector assembly 64 is made from Bayer Makrolen Rx1805 with a surface finish defined as SPI/SPE A-3.

6. Orientation

As before described, $CO_2$ transport is accomplished by two lumens 34 and 36 that extend about 175 degrees about the outer circumference of the sheath 14. For a 0° shaft tip (see FIG. 5A), the orientation of the deflector assembly 64 relative to the laparoscopic lens is not critical. However, for angled shafts (e.g., 30° shaft tips and 45° shaft tips) (see FIG. 5B), the orientation of the deflector assembly 64 relative to the laparoscopic lens is critical.

As FIG. 5B shows, the angled tip of a typical laparoscope 12 has a high end 66 and a low end 68. The lens slopes at the prescribed angle between the high end 66 and the low end 68. In a laparoscope 12 having a angled tip, the illumination cable 30 (transmitting light onto the operating field) is located at the high end 66 of the angled tip, and the camera cable 32 (transmitting reflected light back to the camera) is located at the low end 68 of the angled tip. To provide the desired wind shear effect on an angled tip, it is critical that the deflector assembly 64 be oriented relative to the sloped laparoscopic lens such that the flow $CO_2$ is directed across the sloped plane of the lens from the low end 68 of the tip toward the high end 66 of the tip. In this arrangement, the defogging and debris deflection flow path originates proximal to the camera cable 32, which effectively comprises the eyes of the OR team. In this arrangement, the desired exit angle $A_{EXIT}$ directs the flow path of the $CO_2$ both sufficiently across and proximal to the sloped plane of the laparoscopic lens to achieve optimal defogging and debris deflection.

F. Sterile Fluid Flush

As previously explained, if desired, the tubing set 16 can also include, connected to the quick exchange coupler 22, a length of tubing 70 sized and configured for connection to a source 72 of sterile fluid, such as saline or sterile water (as shown in FIGS. 1A and 2A). Preferably, the sterile fluid includes in solution a "surface-active agent" that stabilizes mixtures of oil and water (e.g., fat) by reducing the surface tension at the interface between the oil and water molecules.

The quick exchange coupling 20 on the manifold 18 (see FIGS. 3A/3B and 4B/4B) can also include a port to integrally connect the sterile fluid tubing 70 to direct the sterile fluid through the separate lumen 38 in the sheath 14 to the distal end of the sheath 14. The deflector assembly 64 directs the sterile fluid across the laparoscopic lens.

As shown in FIGS. 1A/2A, the sterile fluid tubing 70, if present, desirably includes an in-line pumping device 72. The in-line pumping device 72 is sized and configured to be operated on demand by a person at the OR table to convey bursts of sterile fluid through the manifold 18 through the lumen to the distal end of the sheath 14. The in-line pumping device 72 and source can be integrated and comprise, e.g., a 20 cc syringe filled with sterile fluid and connected by a tubing luer-lock on the saline tubing. Alternatively, the in-line pumping device 72 and source can be separate and comprise, e.g., a bag of sterile fluid, a spike connection on the saline tubing of the tubing set 16 to open communication with the bag in conventional fashion, and an inline squeeze bulb or the like to pump burst of sterile fluid from the bag to the quick exchange coupler 22.

In this arrangement, the deflector assembly 64 is also sized and configured to direct the burst of sterile fluid in a desired path across the laparoscopic lens. The bursts of sterile fluid serve to flush debris off the end of the lens that may eventually accumulate, thereby cleaning the lens. Thereafter, bursts of air supplied through the deflector assembly 64 by a squeeze pump 74 in the tubing set 16 (see FIGS. 1A/2A) serve to clear residual fluid droplets off the lens and away from the deflector assembly 64 to maintain the desired flow path and flow velocity of $CO_2$ established by the deflector assembly 64 continuously across the laparoscopic lens, to maintain an acceptable view.

In an illustrative embodiment (see FIGS. 5A and 5B), the deflector assembly 64 directs the bursts of sterile fluid or air along a plurality of individual diverging channels 76 (three are shown). The diverging channels 76 distribute the bursts of sterile fluid or air in a fanning pattern across the lens of the laparoscope 12. In the illustrative embodiment, the diverging channels 76 discharge the bursts of sterile fluid or air in a path that is generally ninety-degrees to the path of $CO_2$. This orientation of the sterile fluid path relative to the $CO_2$ path across the lens, optimal for effective lens cleaning, applies to both 0° shaft tips and angled tips (e.g., 30° shaft tips and 45° shaft tips).

II. Use of the View Optimizing Assembly

The view optimizing assembly is well suited for use as a single-use disposable laparoscopic accessory device to facilitate intra-operative defogging and debris deflection (due to the flow of anhydrous $CO_2$) and cleaning of the lens of a laparoscope 12 (due to burst of sterile fluid, preferably including a "surface-active agent") during minimally invasive surgery, while also maintaining visualization of the surgical site.

FIGS. 7 to 34 illustrate a representative method including the set up and use of the view optimizing assembly using sterile technique by qualified technicians/operating room personnel.

The procedure can be incorporated into written instructions for use that accompany the packaging. The instructions can also be supplied separately, e.g., embodied in separate instruction manuals, or in video or audio tapes, CD's, and DVD's. The instructions for use can also be available through an internet web page.

The instructions can direct the OR set-up to peel open the outer pouches in which the components of the view optimizing assembly (shown in FIG. 7), and remove the sterile contents on the sterile field. The sheath 14/manifold 18 assembly is removed, taking care to prevent damage to the walls of the sheath 14 or to its distal end, and also keeping the tubing set 16 and vent device 24 on the sterile field prior to making necessary connections.

During set up (see FIGS. 8 and 9), the sheath 14 (with the manifold 18, which is integrally connected to the sheath 14 during manufacture, called a sheath assembly) can be assembled to the corresponding laparoscope 12. In this representative example, it is contemplated that the OR team plan to use a 0-degree laparoscope 12 (see FIGS. 8 and 9) and at least one angled laparoscope 12 (see FIGS. 10 and 11), e.g., a 30-degree and/or a 45-degree laparoscope 12. Therefore, during set-up, a sheath assembly for each laparoscope 12 selected for use will be pre-assembled to the corresponding laparoscope 12.

Figure 8:
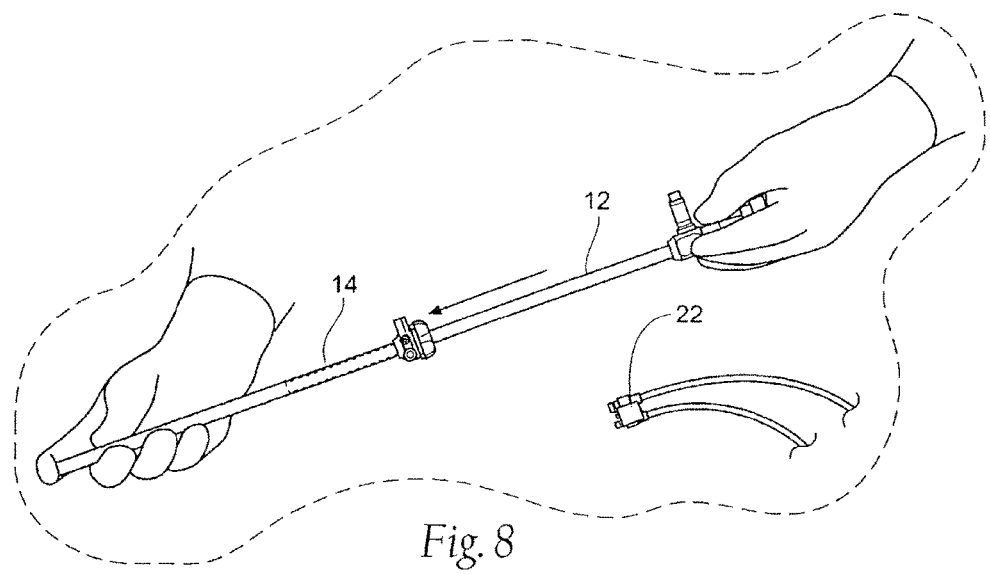
Figure 9:
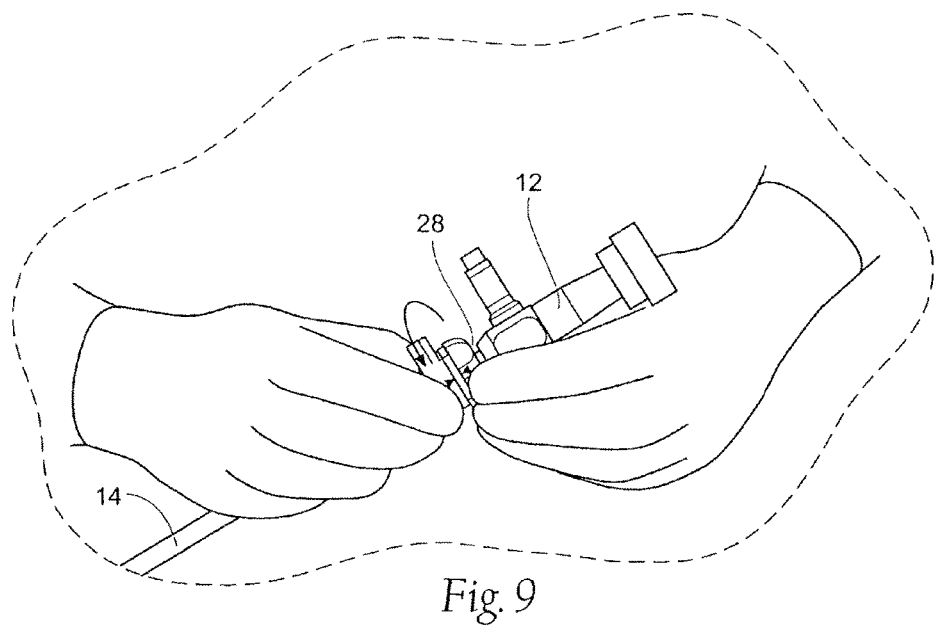
Figure 10:
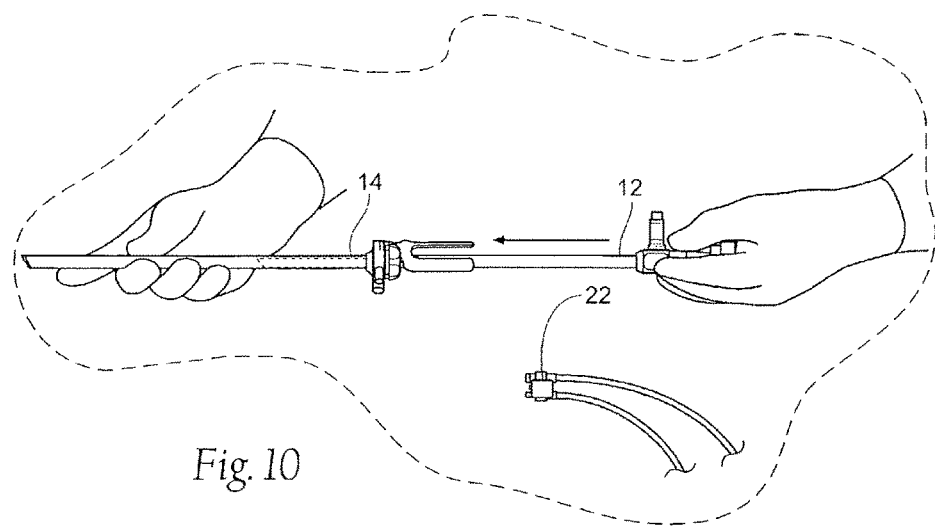
Figure 11:
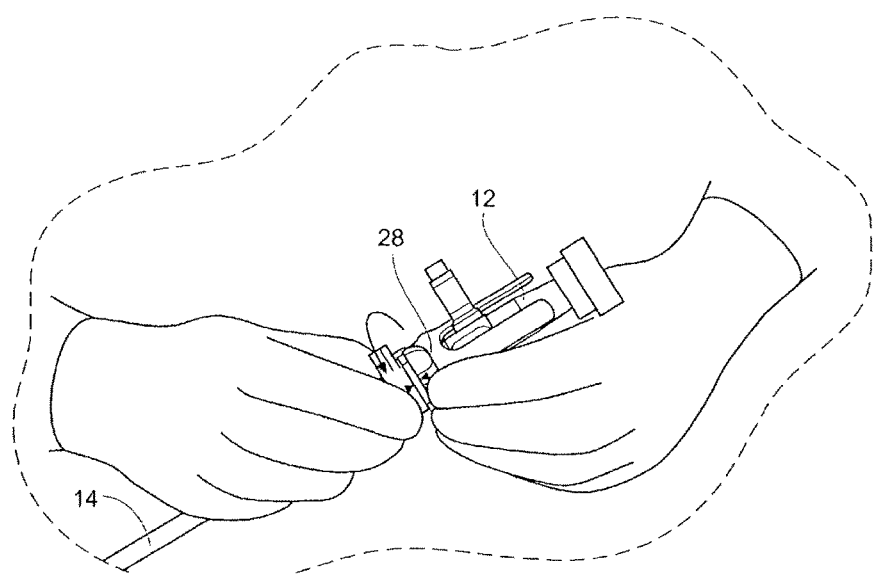

As FIGS. 8 and 10 show, while gently pressing the tip of the sheath assembly against one hand or finger-tip, the laparoscope 12 can be inserted down into the sheath 14. The sheath 14 is sized and configured so that the laparoscope 12 will slide smoothly through the sheath 14. Insertion continues until the lens and distal rim of the laparoscope 12 seat against the stop at the distal end of the sheath 14. The laparoscope 12 will "bottom out" inside the sheath 14 against the stop 26, assuring correct axial alignment of the lens with the deflector assembly 64.

If the laparoscope 12 is angled (as shown in FIG. 10), the corresponding sheath assembly will also include an alignment fork guide 78. The light post of the scope seats within the alignment fork guide 78, therefore assuring correct rotational alignment between the angled lens and the deflector assembly 64.

The laparoscope 12 (now fully inserted into the sheath 14) the manifold 18 are supported by hand, a member of the OR set-up team rotates the locking collar 28 on the sheath assembly in the desired direction, e.g., clockwise (see FIGS. 9 and 11), indicated by an arrow on the locking collar 28, until a firm stop is felt tactilely (e.g., after approximately one-third (⅓) of a turn). Registration of an alignment mark on the locking collar 28 and an alignment mark on the manifold 18 serves to visually confirm that the laparoscope 12 is secured against axial movement relative to the sheath 14.

The insufflator is set up off the sterile field. Once the patient is draped on the sterile field, and it is expected that the end of the output tubing from the insufflator (originating from the insufflator off the sterile field) will brought onto the sterile field. It is also expected that the light cable 30 and the camera cable 32 for the laparoscope 12 will be brought onto the sterile field.

Figure 12:
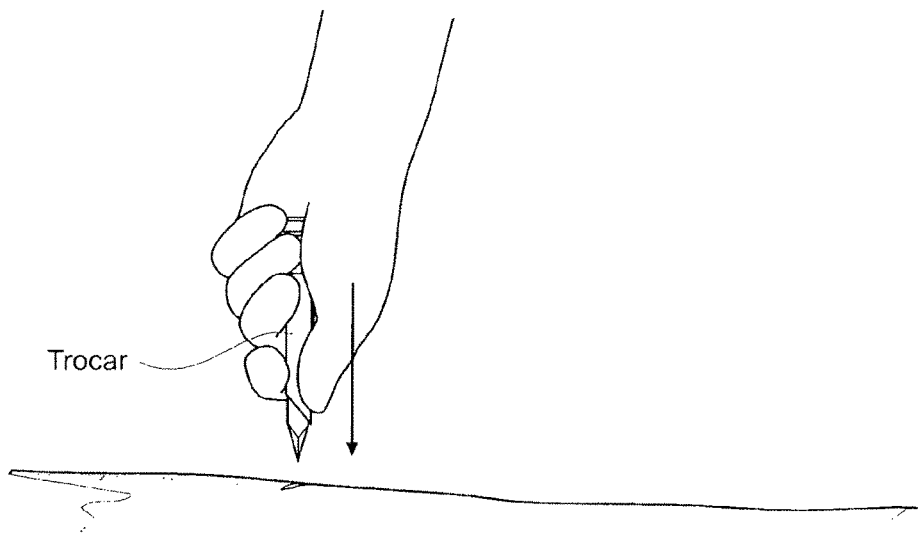
Figure 13:
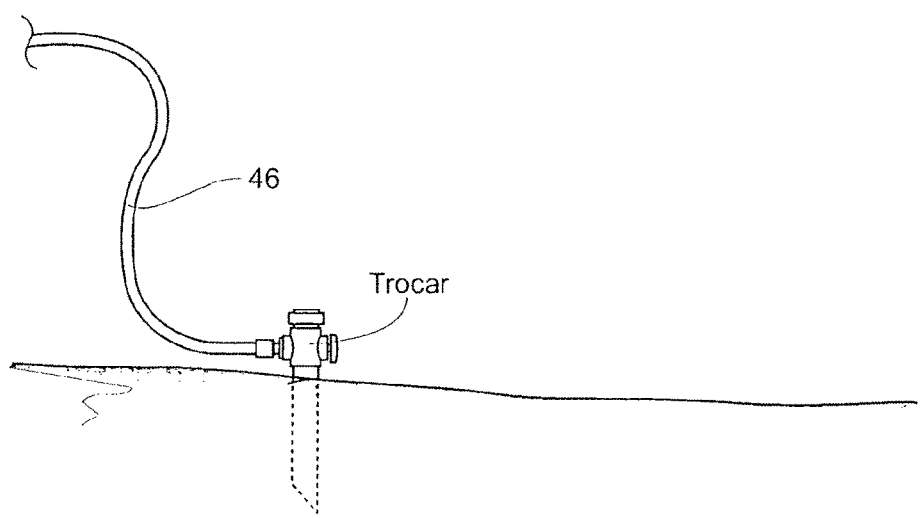

As FIGS. 12 and 13 generally show, the OR team makes an incision to gain access to the laparoscopic operating site within the body, e.g., into the abdominal cavity through the abdominal wall. A first trocar with a stopcock valve (which may take the form of an optical trocar) is inserted through the incision. Alternatively, according to physician preference, the first trocar can be pushed through abdominal wall with only a skin incision. The obturator (the sharp inner insert of the trocar) is removed from the first trocar once it is in position.

The insufflator line of the tubing set 16 on the sterile field is connected to the output tubing of the insufflator circuit on the sterile field. The first branch 46 of the tubing set 16 on the sterile field, originating at the Y-connector 44, is coupled to the stopcock valve of the first trocar (see FIG. 13). The stopcock valve is opened, and the insufflator is turned on. $CO_2$ output of the insufflation circuit inflates the abdomen through the first trocar.

During this time (see FIGS. 8 and 10), the second branch 48 of the tubing set 16 on the sterile field, also originating at the Y-connector 44, and the quick exchange coupler 22 integrally attached to it can remain on the sterile field in a free, unconnected condition as the insufflator supplies $CO_2$ through the first branch 46. The one-way check valve in the quick exchange coupler 22 serves to block flow of $CO_2$ through the second branch 48, even as the insufflator supplies $CO_2$ through the first branch 46. The entire $CO_2$ pressure of the insufflator circuit is, at the present, delivered to the first trocar through the first branch 46.

The first laparoscope 12 selected for use, which has been pre-inserted into the sheath 14 by the OR set-up team as just described, is handed to personnel at the OR table at the appropriate time. On the sterile field, personnel at the OR table connect the light cable 30 and the camera cable 32 to the laparoscope 12 (see FIG. 14). On the sterile field, personnel at the OR table now connect the quick exchange coupler 22 of the tubing set 16 to the quick exchange coupling 20 of the manifold 18 (see FIG. 15). The one way valve opens, and a small portion of the output of the insufflator circuit is routed by the second branch 48 through the manifold 18 into to the sheath 14.

The laparoscope/sheath assembly is then placed as an integrated unit through the first trocar to get an initial view of the abdominal cavity (see FIG. 16). Due to the technical features of the deflector assembly 64, $CO_2$ flows over the lens, eliminating fogging and also deflecting away debris. If present, the pump (e.g., the 20 cc syringe) filled with sterile fluid (preferably with a "surface-active agent") and connected to the tubing luer-lock, can be operated by personnel at the OR table to flush sterile fluid through the deflector assembly 64 of the sheath 14. The deflector assembly 64 directs the fluid bursts across the lens in a path generally 90-degrees offset from the $CO_2$ path. Once this is done, the bulb on the tubing set 16 can be pumped several times introduce bursts of air to clear droplets off the lens and away from the tip deflector, to maintain to the continuous directed flow of $CO_2$ across the laparoscopic lens.

Figure 17:
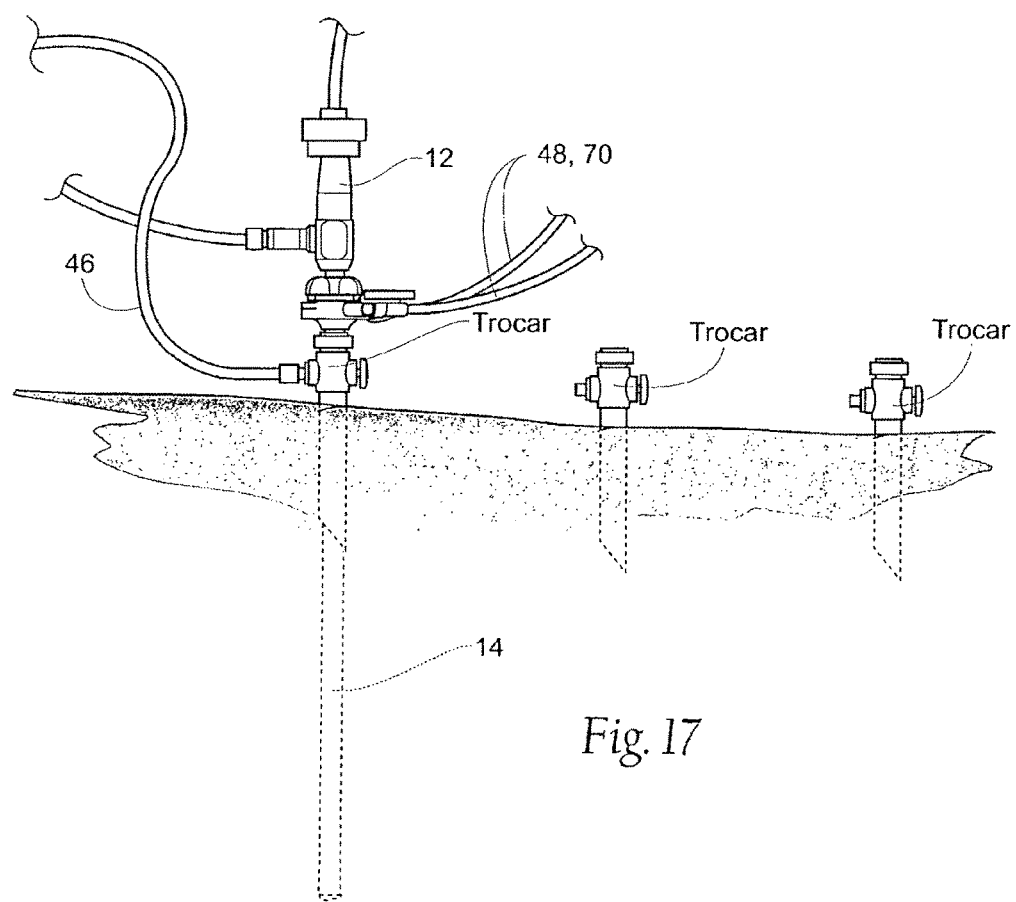
Figure 18:
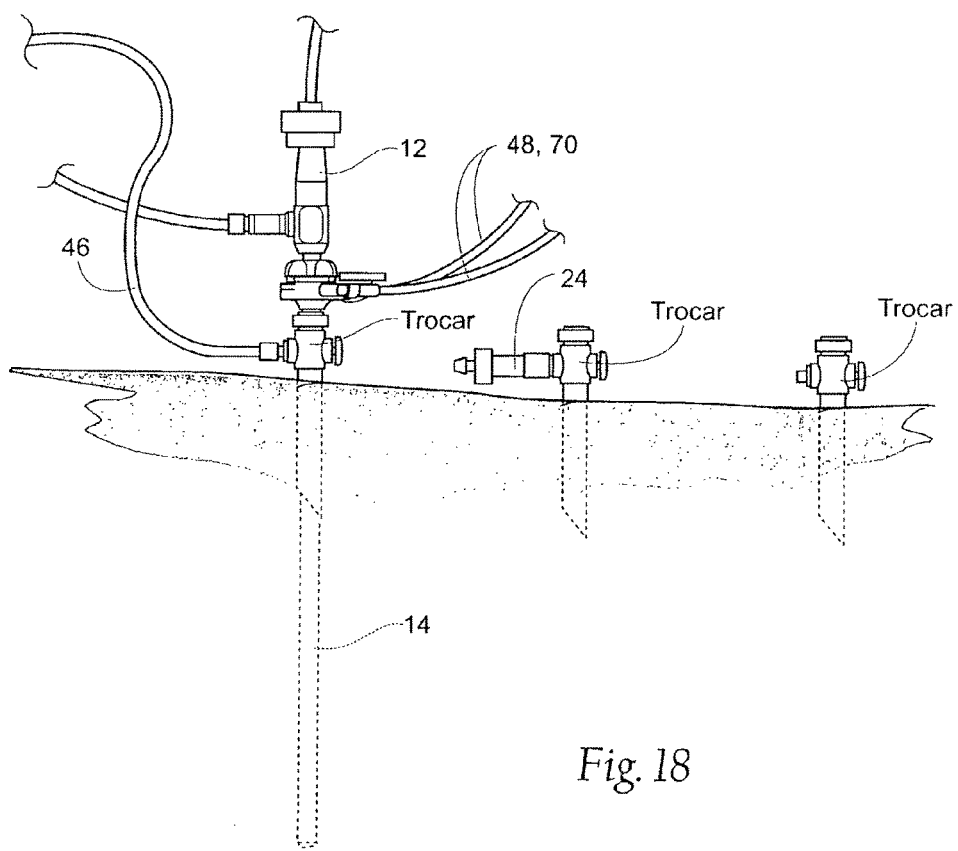

Once a satisfactory view is achieved, additional ancillary trocars with stopcock valves, e.g. three to four, or more, are also placed through incisions to provide access for other instruments (see FIG. 17). The trocar vent device 24 provided with the view optimizing assembly is desirably placed in the stopcock of one of the ancillary trocars, and the stopcock valve is opened (see FIG. 18).

Figure 19:
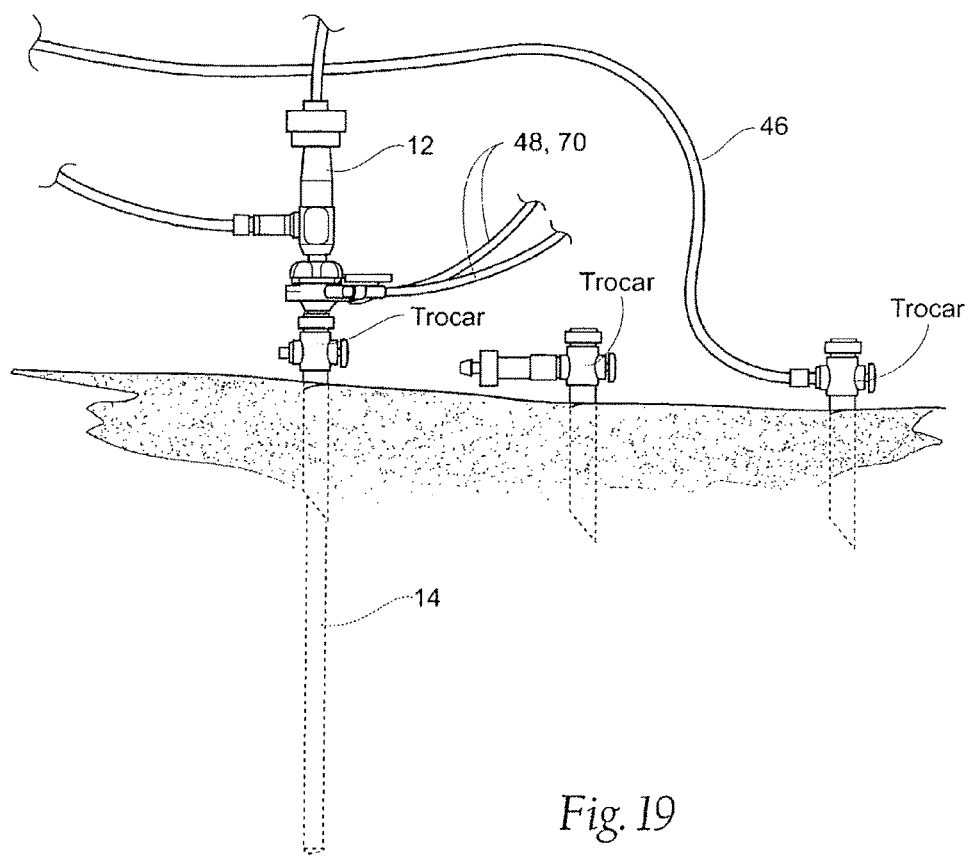

As FIG. 19 shows, a member of the OR team preferable decouples the main insufflation line (the first branch 46 tubing of the Y-connector 44 of the tubing set 16) from the first trocar to the stopcock valve of another available trocar on the sterile field (except the trocar to which the vent device 24 is coupled). This other trocar then serves as the main insufflation trocar, separate from the first trocar, which now serves as the main visualization trocar. In this way, the main $CO_2$ insufflation provided for the duration of the surgery is provided by an insufflation trocar that is also not the visualization trocar. The controlled leak of insufflation pressure that the vent device 24 provides creates a pressure gradient within the pneumo-peritoneum that helps maintain a generally continuous flow of $CO_2$ from the deflector assembly 64 across the lens, despite periodic cycling of the insufflator. Lumens 40 and 42 in the sheath 14 (previously described) can also serve as additional passive vents, to leak insufflation pressure out through the manifold 18.

The surgery proceeds. The deflector assembly 64 provides intra-operative defogging and cleaning of the laparoscope lens during the minimally invasive surgery, while maintaining visualization of the surgical site. The sterile fluid flush mechanism can be used, as desired, if required to augment visualization by flushing the lens. If this is done, the bulb on the tubing set 16 should be pumped several times to clear droplets off the lens and away from the deflector assembly 64 to maintain the $CO_2$ curtain across the lens.

During the surgery, the OR team can decide, e.g., that one portion of the procedure is better visualized with a different angle scope. The quick exchange features of the coupler of the tubing set 16 and the coupling of the manifold 18, greatly facilitate the exchange of one laparoscope 12 for another with minimal interruption of the surgical procedure and without compromising the sterile field.

Figure 20:
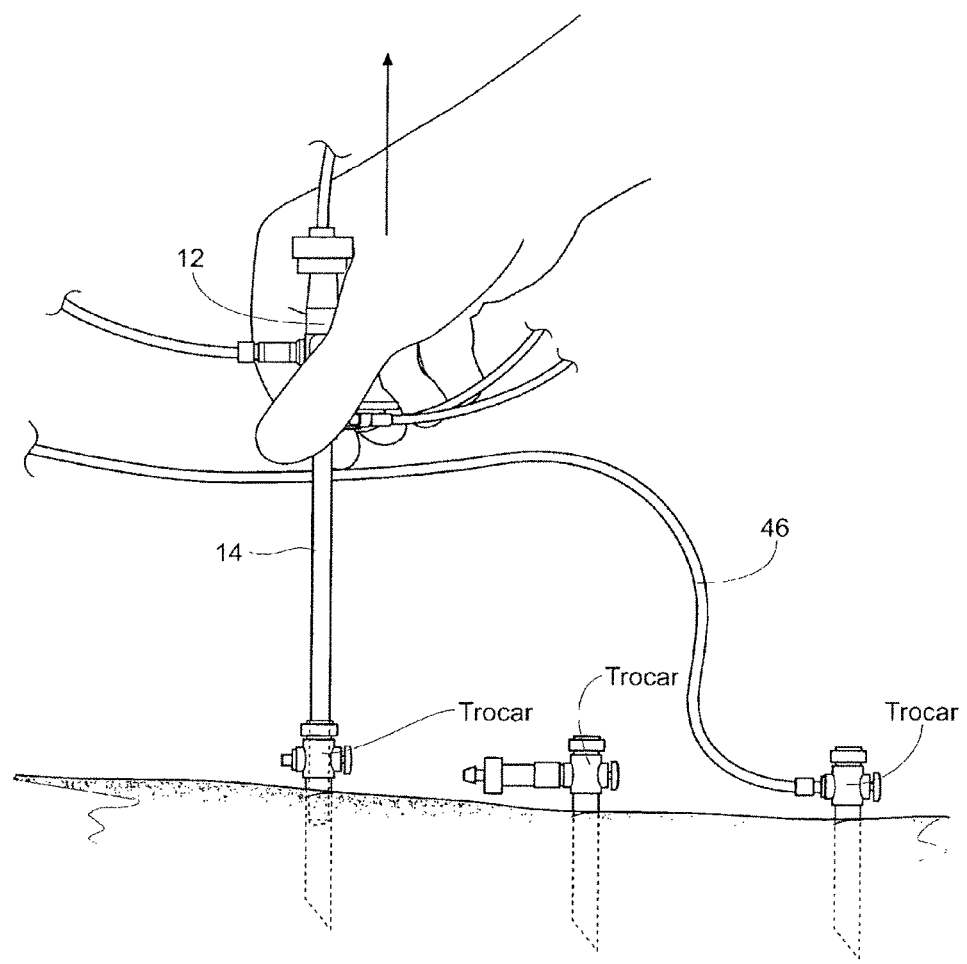
Figure 21:
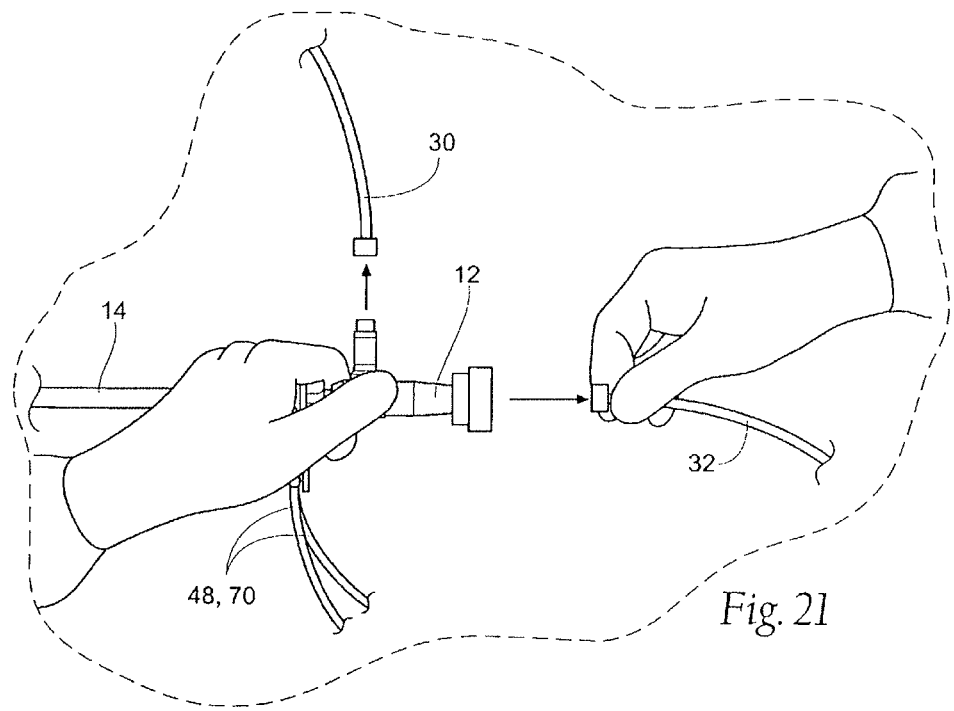

To exchange one laparoscope 12 for another, a member of the OR team withdraws the laparoscope/sheath assembly an integrated unit from the visualization trocar (see FIG. 20). A member of the OR team disconnects the laparoscope 12 from the light cable 30 and camera cable 32 (see FIG. 21). A member of the OR team uncouples the quick exchange coupler 22 from the quick exchange coupling 20, freeing the laparoscope/sheath assembly from the tubing set 16 (see FIG. 22). The disconnected laparoscope/sheath assembly is handed as an integrated unit to a member of the OR team, e.g., a scrub nurse (see FIG. 23). There is no reason to remove the sheath 14 from the matching laparoscope 12 at this time. This can be accomplished later, after the surgery is all done.

The laparoscope/sheath assembly that includes the second laparoscope 12 that is to be used, has already been assembled into an integrated unit, as previously described. This pre-assembled unit is handed to a member of the OR team (see FIG. 24). A member of the OR team connects the second laparoscope 12 to the light cable 30 and camera cable 32 (see FIG. 25). A member of the OR team couples the quick exchange coupler 22 of the tubing set 16 to the quick exchange coupling 20, connecting the second laparoscope/sheath assembly in flow communication with the tubing set 16 (see FIG. 26), completing the quick exchange. The second laparoscope/sheath assembly is inserted into the visualization trocar (see FIG. 27).

The quick connect feature functions with a manifold 18 associated with every sheath 14. The tubing set 16 on the sterile field can be rapidly disconnected, but need not, and desirably is not, exchanged with another tubing set 16. During a given surgical procedure, the same tubing set 16 serves every laparoscope/sheath assembly used (unneeded tubing sets 16 that came with the additional sheaths can be simply discarded).

The surgery proceeds using the second laparoscope/sheath assembly.

Additional quick exchanges of laparoscopes can be accomplished as surgery proceeds in the manner just described.

Figure 28:
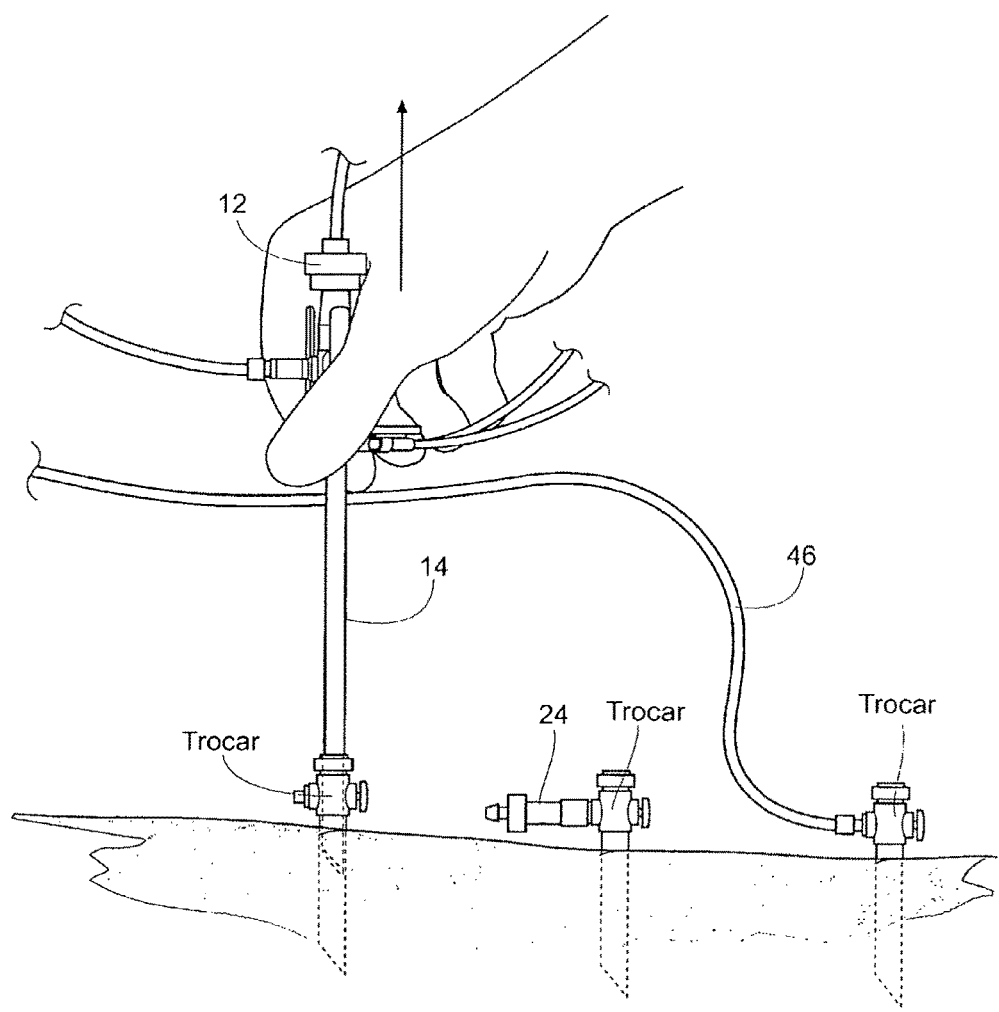
Figure 29:
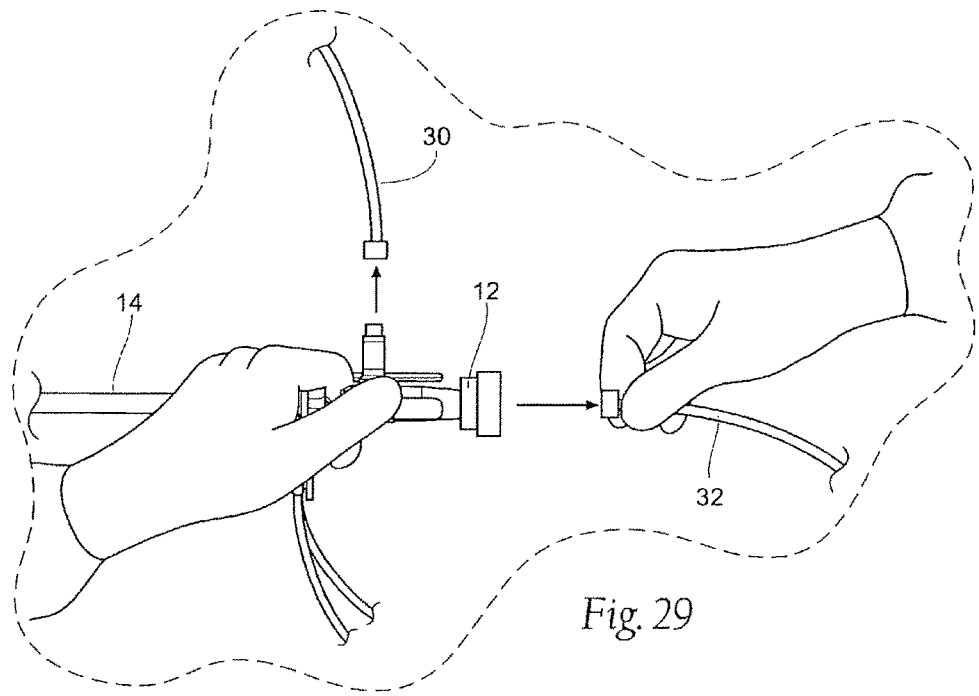
Figure 30:
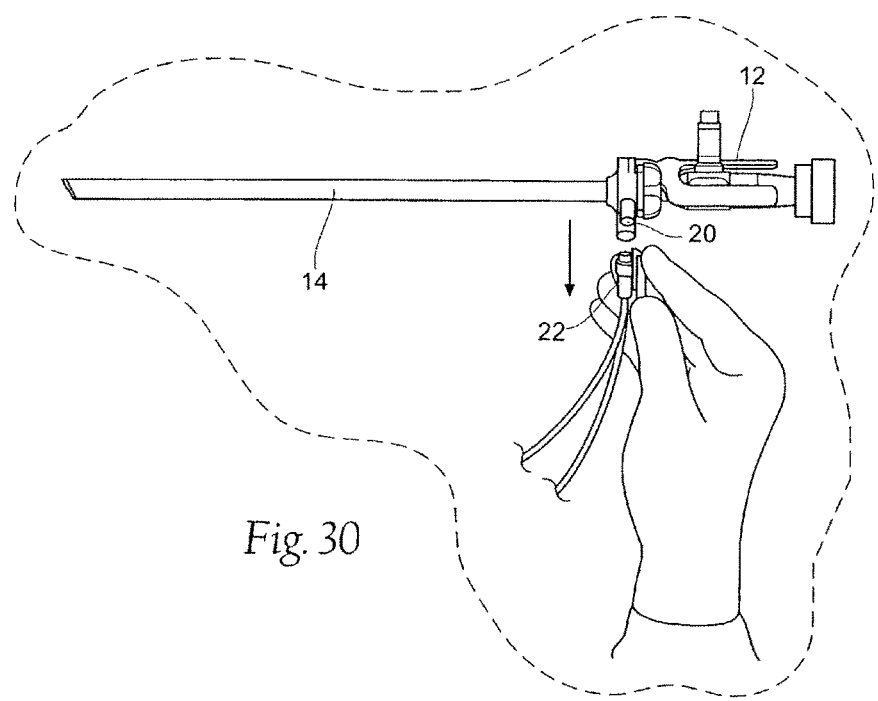
Figure 31:
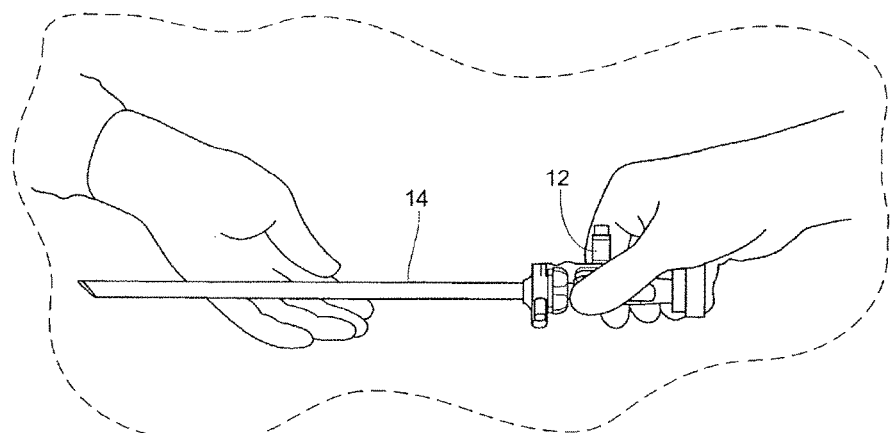
Figure 32:
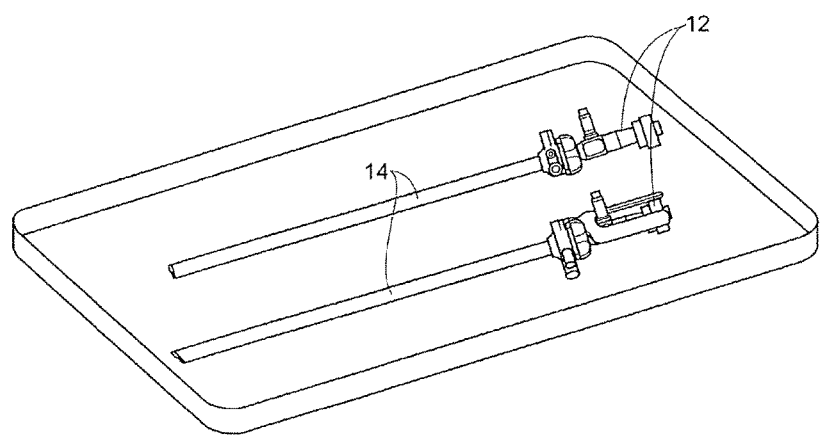

Once surgery is completed, all instruments, including the laparoscope/sheath assembly in use are removed from the visualization trocar (see FIG. 28). A member of the OR team disconnects the laparoscope 12 from the light cable 30 and camera cable 32 (see FIG. 29). A member of the OR team uncouples the quick exchange coupler 22 from the quick exchange coupling 20, freeing the laparoscope/sheath assembly from the tubing set 16. The laparoscope/sheath assembly is handed to a member of the OR team (see FIG. 31), and placed alongside previously used laparoscope/sheath assemblies (see FIG. 32).

Figure 33:
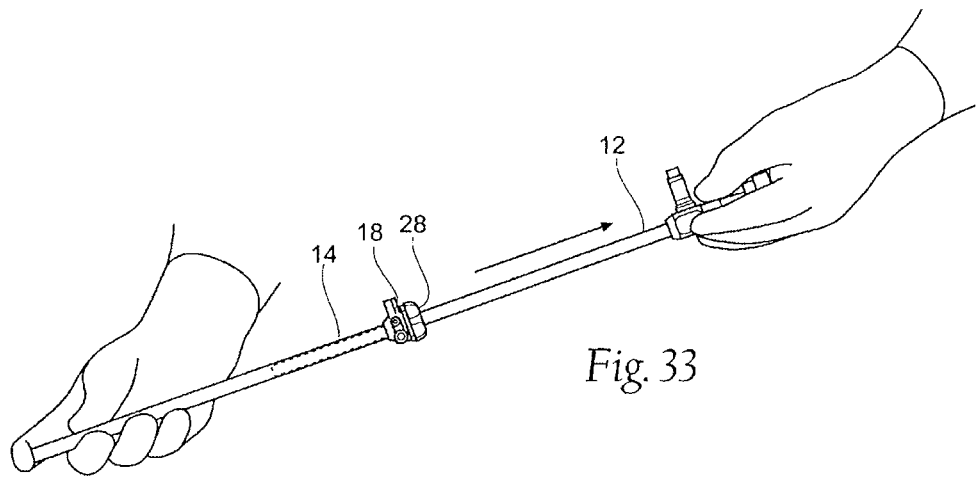
Figure 34:
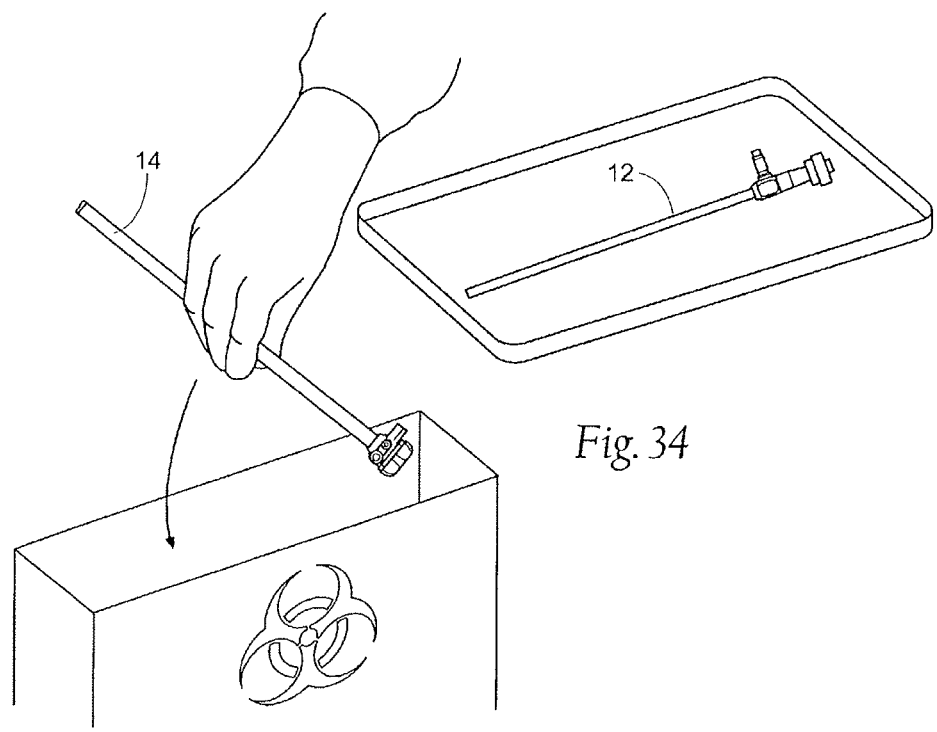

Access sites are closed. The insufflator is shut off. The tubing set 16 is disconnected from the insufflator circuit. The lock collars on the manifolds 18 are loosened, and laparoscopes are withdrawn from the sheaths for reuse (FIG. 33). The sheaths and tubing set 16 are disposed of (FIG. 34).

Some trocars are called "optical trocars" that have a lumen within the obturator, that is within the trocar. If the lens of a laparoscope 12 is first placed into the center of an optical trocar to guide the first trocar insertion, then the sheath 14 cannot be present on the laparoscope 12, as the combination cannot fit through the lumen of the obturator. In this situation, the laparoscope 12 is used without a sheath 14 is used to place the first trocar. The laparoscope 12 is then inserted through the sheath 14, and connection of the tubing set 16 occurs in the manner just described. With the obturator removed from the trocar, the laparoscope/sheath assembly is placed through the first trocar in the manner described.

What is claimed is:

1. A method of defogging and cleaning a laparoscope, comprising:
    inserting a laparoscope into a sheath;
    inserting the laparoscope and sheath into a body cavity;
    connecting a tubing set to the sheath and to an insufflator;
    pressurizing the body cavity with gas from the insufflator;
    while the cavity is inflated, routing a portion of the gas from the insufflator through the tubing set to a plurality of gas lumens within a wall of the sheath such that the gas flows continuously through the gas lumens and directly over a lens of the laparoscope at a base flow rate of at least 1.0 liters per minute while the insufflator is on to defog the lens while the laparoscope is in the body cavity;
    providing a fluid comprising a surface-active agent to a fluid lumen within the wall of the sheath such that the fluid flows through the fluid lumen and over the lens to clean the lens while the laparoscope is in the body cavity; and
    after the providing a fluid step, providing a burst of air through the tubing set and over the lens to clear the fluid off of the lens while the laparoscope is in the body cavity.

2. The method of claim 1, wherein the fluid is from a syringe coupled with the sheath.

3. The method of claim 1, further comprising deflecting the gas from distal ends of the gas lumens over the lens with a deflector connected to a distal end of the sheath.

4. The method of claim 3, wherein inserting the laparoscope into the sheath comprises inserting the laparoscope into the sheath until the laparoscope hits a stop on the deflector.

5. The method of claim 1, further comprising deflecting the fluid from a distal end of the fluid lumen over the lens with a deflector connected to a distal end of the sheath.

6. The method of claim 5, wherein inserting the laparoscope into the sheath comprises inserting the laparoscope into the sheath until the laparoscope hits a stop on the deflector.

7. The method of claim 1, further comprising locking the laparoscope in place relative to the sheath.

8. The method of claim 1, further comprising venting air from the body cavity through a trocar to provide a pressure gradient within the body cavity to maintain a continuous flow of gas from the gas lumens over the lens.

9. The method of claim 1, wherein the surface active agent stabilizes mixtures of oil and water on the lens within the body cavity by reducing surface tension at the interface between the oil and water molecules.

10. The method of claim 1, wherein pressurizing the body cavity with gas from the insufflator comprises flowing gas through the tubing set to a trocar within the body cavity.

11. The method of claim 1, wherein providing a fluid comprising a surface-active agent to a fluid lumen comprises providing a fluid through the tubing set to the fluid lumen.

* * * * *